US010369349B2

(12) United States Patent
Nelson

(10) Patent No.: US 10,369,349 B2
(45) Date of Patent: Aug. 6, 2019

(54) MEDICAL FLUID MANIFOLD

(71) Applicant: ICU MEDICAL, INC., San Clemente, CA (US)

(72) Inventor: David Nelson, Irvine, CA (US)

(73) Assignee: ICU MEDICAL, INC., San Clemente, CA (US)

( * ) Notice: Subject to any disclaimer, the term of this patent is extended or adjusted under 35 U.S.C. 154(b) by 351 days.

(21) Appl. No.: 15/179,760

(22) Filed: Jun. 10, 2016

(65) Prior Publication Data

US 2016/0279404 A1 Sep. 29, 2016

Related U.S. Application Data

(63) Continuation of application No. PCT/US2014/068455, filed on Dec. 3, 2014.
(Continued)

(51) Int. Cl.
*A61M 39/10* (2006.01)
*A61M 39/24* (2006.01)
(Continued)

(52) U.S. Cl.
CPC .......... *A61M 39/24* (2013.01); *A61M 5/1408* (2013.01); *A61M 39/10* (2013.01);
(Continued)

(58) Field of Classification Search
CPC .................. A61M 39/22; A61M 39/24; A61M 2039/2406; A61M 2039/242; A61M 2039/2426; A61M 2039/2433; A61M 2039/2446; A61M 2039/2453; A61M 5/1408; A61M 2039/246; A61M 39/26; A61M 2039/2466; F16K 15/00;
(Continued)

(56) References Cited

U.S. PATENT DOCUMENTS 274,447 A 3/1883 Kennish
1,578,517 A 3/1926 Hein
(Continued)

FOREIGN PATENT DOCUMENTS

CA 1 105 959 7/1981
CA 2 149 725 11/1995
(Continued)

OTHER PUBLICATIONS

U.S. Appl. No. 29/510,851, filed Dec. 3, 2014, Nelson.
(Continued)

*Primary Examiner* — Bhisma Mehta
*Assistant Examiner* — James D Ponton
(74) *Attorney, Agent, or Firm* — Knobbe, Martens, Olson & Bear, LLP

(57) ABSTRACT

A medical manifold for use in providing access to a fluid flow path. The medical manifold can include a valve member having a diaphragm and first and second support members extending from a bottom surface of the diaphragm. The first and second support members can be positioned to define a line of symmetry that's bisects the bottom surface of the diaphragm. The diaphragm can have a first position in which a top surface thereof is generally planar and a second position in which the diaphragm is flexed downward around the line of symmetry.

19 Claims, 20 Drawing Sheets

Related U.S. Application Data

(60) Provisional application No. 61/914,892, filed on Dec. 11, 2013.

(51) Int. Cl.
*A61M 39/26* (2006.01)
*A61M 5/14* (2006.01)
*F16K 15/14* (2006.01)

(52) U.S. Cl.
CPC .......... *A61M 39/26* (2013.01); *F16K 15/144* (2013.01); *A61M 2039/2446* (2013.01); *A61M 2039/2453* (2013.01); *A61M 2039/267* (2013.01); *A61M 2207/00* (2013.01)

(58) Field of Classification Search
CPC .... F16K 15/141; F16K 15/144; F16K 15/148; F16K 7/20
See application file for complete search history.

(56) References Cited

U.S. PATENT DOCUMENTS 1,923,501 A 8/1933 Perry
2,210,098 A 8/1940 Ravenscroft
2,289,677 A 7/1942 Perelson
2,577,780 A 12/1951 Lockhart
2,756,282 A 7/1956 Deane
2,756,740 A 7/1956 Deane
2,809,665 A 10/1957 Crowe
2,847,995 A 8/1958 Adams
2,999,499 A 9/1961 Willet
3,134,380 A 5/1964 Armao
3,135,261 A 6/1964 Carroll
3,171,412 A 3/1965 Braun
3,176,021 A 3/1965 Volungis et al.
3,191,655 A 6/1965 McCord
3,193,154 A 7/1965 Bross et al.
3,334,860 A 8/1967 Bolton, Jr.
3,352,531 A 11/1967 Kilmarx
3,354,881 A 11/1967 Bloch
3,385,301 A 5/1968 Harautuneian
3,502,097 A 3/1970 Muller
3,534,771 A 10/1970 Eyerdam et al.
3,570,484 A 3/1971 Steer et al.
3,630,199 A 12/1971 Gangarosa
3,648,684 A 3/1972 Barnwell et al.
3,659,602 A 5/1972 Cloyd
3,717,174 A 2/1973 Dewall
3,726,282 A 4/1973 Patel
3,788,519 A 1/1974 Mengel
3,830,241 A 8/1974 Dye et al.
3,831,629 A 8/1974 Mackal et al.
3,852,385 A 12/1974 Huggins
3,861,388 A 1/1975 Vaughn
3,889,675 A 6/1975 Stewart
3,896,853 A 7/1975 Bernhard
3,965,910 A 6/1976 Fisher
3,974,832 A 8/1976 Kruck
3,976,063 A 8/1976 Henneman et al.
3,976,073 A 8/1976 Quick et al.
3,977,403 A 8/1976 Patel
3,986,508 A 10/1976 Barrington
3,993,063 A 11/1976 Larrabee
3,994,293 A 11/1976 Ferro
4,005,710 A 2/1977 Zeddies et al.
4,019,512 A 4/1977 Tenczar
4,022,205 A 5/1977 Tenczar
4,040,420 A 8/1977 Speer
4,076,285 A 2/1978 Martinez
4,079,738 A 3/1978 Dunn et al.
4,080,965 A 3/1978 Phillips
4,121,585 A 10/1978 Becker, Jr.
4,128,098 A 12/1978 Bloom et al.
4,133,441 A 1/1979 Mittleman et al.
4,143,853 A * 3/1979 Abramson ............ A61M 39/26 137/515.7
4,149,535 A 4/1979 Volder
4,161,949 A 7/1979 Thanawalla
4,186,775 A 2/1980 Muroi
4,187,846 A 2/1980 Lolachi et al.
4,191,183 A 3/1980 Mendelson
4,198,983 A 4/1980 Becker et al.
4,200,096 A 4/1980 Charvin
4,214,779 A 7/1980 Losell
4,219,912 A 9/1980 Adams
4,243,034 A 1/1981 Brandt
4,257,416 A 3/1981 Prager
D259,278 S 5/1981 McCaw et al.
4,294,249 A 10/1981 Sheehan et al.
4,294,250 A 10/1981 Dennehey
4,296,949 A 10/1981 Muetterties et al.
4,306,705 A 12/1981 Svensson
D263,871 S 4/1982 Matsuura
4,324,239 A 4/1982 Gordon et al.
4,328,802 A 5/1982 Curley et al.
4,329,987 A 5/1982 Rogers et al.
4,334,551 A 6/1982 Pfister
4,338,933 A 7/1982 Bayard et al.
4,342,315 A 8/1982 Jackson
4,346,703 A 8/1982 Dennehey et al.
4,362,156 A 12/1982 Feller et al.
4,387,879 A 6/1983 Tauschinski
RE31,315 E 7/1983 Jenkins et al.
4,392,851 A 7/1983 Elias
4,405,163 A 9/1983 Voges et al.
4,405,312 A 9/1983 Gross et al.
4,411,662 A 10/1983 Pearson
4,417,890 A 11/1983 Dennehey et al.
4,421,296 A 12/1983 Stephens
4,429,856 A 2/1984 Jackson
4,432,759 A 2/1984 Gross et al.
4,432,765 A 2/1984 Oscarsson
4,439,188 A 3/1984 Dennehey et al.
4,439,193 A 3/1984 Larkin
4,449,693 A 5/1984 Gerea
4,457,749 A 7/1984 Bellotti et al.
4,483,368 A 11/1984 Panthafer
4,508,367 A 4/1985 Oreopoulos et al.
4,511,359 A 4/1985 Vaillancourt
4,512,766 A 4/1985 Vaillancourt
4,535,820 A * 8/1985 Raines .................. A61M 39/24 137/854
4,556,086 A * 12/1985 Raines .................. F16K 15/141 137/843
4,564,054 A 1/1986 Gustavsson
4,566,480 A 6/1986 Parham
4,592,356 A 6/1986 Guiterrez
4,607,868 A 8/1986 Harvey et al.
4,610,469 A 9/1986 Wolff-Mooij
4,617,012 A 10/1986 Vaillancourt
4,619,640 A 10/1986 Poholshy et al.
4,623,068 A 11/1986 Brown et al.
4,645,494 A 2/1987 Lee et al.
4,666,429 A 5/1987 Stone
4,673,400 A 6/1987 Martin
4,676,228 A 6/1987 Krasner et al.
4,683,916 A 8/1987 Raines
4,706,487 A 11/1987 Bandou et al.
4,710,168 A 12/1987 Schwab et al.
4,725,267 A 2/1988 Vaillancourt
4,730,635 A 3/1988 Linden
4,752,292 A 6/1988 Lopez et al.
D296,592 S 7/1988 Wellenstam
4,758,224 A 7/1988 Siposs
4,759,756 A 7/1988 Forman et al.
4,775,369 A 10/1988 Schwartz
4,778,447 A 10/1988 Velde et al.
4,778,453 A 10/1988 Lopez
4,781,702 A 11/1988 Herrli
4,804,015 A 2/1989 Albinsson
D300,177 S 3/1989 Bellotti et al.
D300,361 S 3/1989 Tokarz
4,810,241 A 3/1989 Rogers et al.

(56) References Cited

U.S. PATENT DOCUMENTS

| | | | | |
|---|---|---|---|---|
| 4,813,938 | A | | 3/1989 | Raulerson |
| 4,819,684 | A | | 4/1989 | Zaugg et al. |
| 4,832,214 | A | | 5/1989 | Schrader et al. |
| 4,834,664 | A | | 5/1989 | Lin |
| 4,834,716 | A | | 5/1989 | Ogle, II |
| D303,013 | S | | 8/1989 | Konopka |
| 4,871,353 | A | | 10/1989 | Thomsen |
| 4,874,377 | A | | 10/1989 | Newgard et al. |
| 4,878,897 | A | | 11/1989 | Katzin |
| 4,880,414 | A | | 11/1989 | Whipple |
| 4,889,527 | A | | 12/1989 | Herrli |
| 4,908,018 | A | * | 3/1990 | Thomsen ............ A61M 5/1408 137/903 |
| 4,915,687 | A | | 4/1990 | Sivert |
| 4,917,668 | A | | 4/1990 | Haindl |
| 4,919,167 | A | | 4/1990 | Manska |
| 4,928,212 | A | | 5/1990 | Benavides |
| 4,934,657 | A | | 6/1990 | Dodson |
| 4,943,896 | A | | 7/1990 | Johnson |
| 4,946,445 | A | | 8/1990 | Lynn |
| 4,946,448 | A | * | 8/1990 | Richmond ............ A61M 39/24 137/493.9 |
| 4,963,133 | A | | 10/1990 | Whipple |
| 4,964,855 | A | | 10/1990 | Todd et al. |
| 4,966,199 | A | | 10/1990 | Ruschke |
| 4,969,883 | A | | 11/1990 | Gilbert et al. |
| D314,050 | S | | 1/1991 | Sone |
| 4,985,399 | A | | 1/1991 | Matsuda et al. |
| 4,987,181 | A | | 1/1991 | Bichon et al. |
| 4,991,413 | A | | 2/1991 | Arnalda |
| 4,991,629 | A | | 2/1991 | Ernesto et al. |
| 4,998,713 | A | | 3/1991 | Vaillancourt |
| 4,998,927 | A | | 3/1991 | Vaillancourt |
| 5,006,114 | A | | 4/1991 | Rogers et al. |
| 5,009,490 | A | | 4/1991 | Kuono et al. |
| 5,018,532 | A | | 5/1991 | Ethridge, III |
| 5,024,657 | A | | 6/1991 | Needham et al. |
| 5,031,675 | A | | 7/1991 | Lindqren |
| 5,041,087 | A | | 8/1991 | Loo et al. |
| 5,046,456 | A | | 9/1991 | Heyman et al. |
| 5,049,128 | A | | 9/1991 | Duquette |
| D321,250 | S | | 10/1991 | Jepson et al. |
| D321,251 | S | | 10/1991 | Jepson et al. |
| 5,061,253 | A | | 10/1991 | Yoshida |
| 5,064,416 | A | | 11/1991 | Newgard |
| 5,065,783 | A | | 11/1991 | Ogle, II |
| 5,071,411 | A | | 12/1991 | Hillstead |
| 5,098,385 | A | | 3/1992 | Walsh |
| 5,098,405 | A | | 3/1992 | Peterson et al. |
| 5,098,406 | A | | 3/1992 | Sawyer |
| 5,100,394 | A | | 3/1992 | Dudar et al. |
| 5,108,380 | A | | 4/1992 | Heritze et al. |
| 5,114,408 | A | | 5/1992 | Fleischhaker et al. |
| 5,116,361 | A | | 5/1992 | Kim et al. |
| 5,122,123 | A | | 6/1992 | Vaillancourt |
| 5,125,915 | A | | 6/1992 | Berry et al. |
| 5,135,489 | A | | 8/1992 | Jepson et al. |
| 5,137,524 | A | | 8/1992 | Lynn et al. |
| 5,147,333 | A | | 9/1992 | Raines |
| 5,154,703 | A | | 10/1992 | Bonaldo |
| 5,158,554 | A | | 10/1992 | Jepson et al. |
| 5,163,922 | A | | 11/1992 | McElveen, Jr. et al. |
| 5,167,238 | A | | 12/1992 | Newman |
| 5,167,636 | A | | 12/1992 | Clement |
| 5,171,234 | A | | 12/1992 | Jepson et al. |
| 5,180,761 | A | | 1/1993 | Shiao |
| 5,188,620 | A | | 2/1993 | Jepson et al. |
| 5,190,067 | A | | 3/1993 | Paradis et al. |
| 5,199,947 | A | | 4/1993 | Lopez et al. |
| 5,201,717 | A | | 4/1993 | Wyatt et al. |
| 5,201,722 | A | | 4/1993 | Moorehead et al. |
| 5,203,775 | A | | 4/1993 | Frank et al. |
| 5,211,638 | A | | 5/1993 | Dudar et al. |
| 5,215,538 | A | | 6/1993 | Larkin |
| 5,221,271 | A | | 6/1993 | Nicholson et al. |
| 5,224,515 | A | | 7/1993 | Foster et al. |
| 5,242,393 | A | | 9/1993 | Brimhall et al. |
| 5,242,423 | A | | 9/1993 | Goodsir et al. |
| 5,242,425 | A | | 9/1993 | Whine et al. |
| 5,242,432 | A | | 9/1993 | DeFrank |
| 5,251,873 | A | | 10/1993 | Atkinson et al. |
| 5,253,842 | A | | 10/1993 | Huebscher et al. |
| 5,255,676 | A | | 10/1993 | Russo |
| 5,256,155 | A | | 10/1993 | Yerlikaya et al. |
| 5,267,966 | A | | 12/1993 | Paul |
| 5,269,771 | A | | 12/1993 | Thomas et al. |
| 5,273,533 | A | | 12/1993 | Bonaldo |
| 5,280,876 | A | | 1/1994 | Atkins |
| D344,585 | S | | 2/1994 | Morse |
| 5,284,475 | A | | 2/1994 | Mackal |
| 5,290,254 | A | | 3/1994 | Vaillancourt |
| 5,292,308 | A | | 3/1994 | Ryan |
| 5,293,902 | A | | 3/1994 | Lapierie |
| 5,295,657 | A | | 3/1994 | Atkinson |
| 5,295,658 | A | | 3/1994 | Atkinson et al. |
| 5,301,686 | A | | 4/1994 | Newman |
| 5,306,265 | A | | 4/1994 | Ragazzi |
| 5,312,083 | A | | 5/1994 | Ekman |
| 5,312,377 | A | | 5/1994 | Dalhon |
| 5,322,518 | A | | 6/1994 | Schneider |
| 5,324,270 | A | | 6/1994 | Kayon et al. |
| 5,336,192 | A | | 8/1994 | Palestrant |
| 5,342,316 | A | | 8/1994 | Wallace |
| 5,342,326 | A | | 8/1994 | Peppel et al. |
| 5,344,414 | A | | 9/1994 | Lopez et al. |
| 5,348,542 | A | | 9/1994 | Ellis |
| 5,353,837 | A | | 10/1994 | Faust |
| 5,356,375 | A | | 10/1994 | Higley |
| 5,356,396 | A | | 10/1994 | Wyatt et al. |
| 5,360,413 | A | | 11/1994 | Leason et al. |
| 5,380,306 | A | | 1/1995 | Brinon |
| 5,389,086 | A | | 2/1995 | Attermeier et al. |
| 5,398,530 | A | | 3/1995 | Derman |
| 5,401,245 | A | | 3/1995 | Haining |
| D357,736 | S | | 4/1995 | Dye |
| 5,402,826 | A | | 4/1995 | Molnar et al. |
| 5,402,982 | A | | 4/1995 | Atkinson et al. |
| 5,407,437 | A | | 4/1995 | Heimreid |
| 5,409,471 | A | | 4/1995 | Atkinson et al. |
| 5,395,348 | A | | 5/1995 | Ryan |
| 5,411,483 | A | | 5/1995 | Loomas et al. |
| 5,411,499 | A | | 5/1995 | Dudar et al. |
| 5,417,673 | A | | 5/1995 | Gordon |
| 5,439,451 | A | | 8/1995 | Collinson et al. |
| 5,439,452 | A | | 8/1995 | McCarty |
| 5,441,487 | A | | 8/1995 | Vedder |
| 5,442,941 | A | | 8/1995 | Kahonen et al. |
| 5,456,676 | A | | 10/1995 | Nelson et al. |
| 5,462,255 | A | | 10/1995 | Rosen et al. |
| D363,988 | S | | 11/1995 | Dye |
| D364,459 | S | | 11/1995 | Dye |
| D364,460 | S | | 11/1995 | Dye |
| D364,680 | S | | 11/1995 | Dye |
| 5,465,938 | A | * | 11/1995 | Werge .................. A61M 39/04 137/843 |
| 5,470,319 | A | | 11/1995 | Mayer |
| 5,474,544 | A | | 12/1995 | Lynn |
| 5,480,393 | A | | 1/1996 | Bommarito |
| 5,487,731 | A | | 1/1996 | Denton |
| D367,714 | S | | 3/1996 | Pennicook |
| 5,501,426 | A | | 3/1996 | Atkinson et al. |
| 5,501,526 | A | | 3/1996 | Asai et al. |
| D368,737 | S | | 4/1996 | Dunn et al. |
| 5,509,433 | A | | 4/1996 | Paradis |
| 5,514,116 | A | | 5/1996 | Vaillancourt et al. |
| 5,520,665 | A | | 5/1996 | Fleetwood |
| 5,522,804 | A | | 6/1996 | Lynn |
| 5,533,708 | A | | 7/1996 | Atkinson et al. |
| 5,533,996 | A | | 7/1996 | Murphey et al. |
| 5,535,771 | A | | 7/1996 | Purdy et al. |
| 5,535,785 | A | | 7/1996 | Werge et al. |
| 5,540,661 | A | | 7/1996 | Tomisaka et al. |
| 5,549,566 | A | | 8/1996 | Elias et al. |
| 5,549,577 | A | | 8/1996 | Siegel et al. |

(56) References Cited

U.S. PATENT DOCUMENTS 5,549,651 A 8/1996 Lynn
D373,633 S 9/1996 La Motte
5,555,908 A 9/1996 Edwards et al.
5,556,388 A 9/1996 Johlin, Jr.
5,562,632 A 10/1996 Davila et al.
5,569,235 A 10/1996 Ross et al.
5,573,516 A 11/1996 Tyner
5,577,706 A 11/1996 King
5,578,059 A 11/1996 Patzer
5,597,536 A 1/1997 Mayer
5,674,206 A 1/1997 Allton et al.
5,603,706 A 2/1997 Wyatt et al.
5,609,584 A 3/1997 Gettig et al.
5,616,129 A 4/1997 Mayer
5,616,130 A 4/1997 Mayer
5,617,897 A 4/1997 Myers
5,620,424 A 4/1997 Abramson
5,620,434 A 4/1997 Brony
5,624,414 A 4/1997 Boettger
5,632,735 A 5/1997 Wyatt et al.
5,639,810 A 6/1997 Smith, III et al.
5,645,538 A 7/1997 Richmond
5,660,205 A 8/1997 Epstein
5,669,891 A 9/1997 Vaillancourt
5,676,346 A 10/1997 Leinsing
5,685,866 A 11/1997 Lopez
5,690,612 A 11/1997 Lopez et al.
5,690,865 A 11/1997 Kindt-Larsen et al.
5,694,686 A 12/1997 Lopez
5,695,466 A 12/1997 Lopez et al.
5,699,821 A 12/1997 Paradis
5,700,248 A 12/1997 Lopez
5,728,751 A 3/1998 Patnaik
5,730,418 A 3/1998 Feith et al.
5,738,663 A 4/1998 Lopez
5,749,861 A 5/1998 Guala et al.
5,769,825 A 6/1998 Lynn
5,775,671 A 7/1998 Cote, Sr.
5,776,113 A 7/1998 Daugherty et al.
5,782,816 A 7/1998 Werschmidt et al.
5,788,215 A 8/1998 Ryan
5,797,897 A 8/1998 Jepson et al.
5,806,551 A 9/1998 Meloul et al.
5,806,831 A 9/1998 Paradis
5,807,348 A 9/1998 Zinger et al.
D400,263 S 10/1998 Shugart
5,817,068 A 10/1998 Urrutia
5,817,069 A 10/1998 Arnett
5,820,601 A 10/1998 Mayer
5,833,213 A 11/1998 Ryan
5,836,923 A 11/1998 Mayer
5,839,715 A 11/1998 Leinsing
5,843,046 A 12/1998 Motisi et al.
5,846,233 A 12/1998 Lilley et al.
5,865,807 A 2/1999 Blake, III
5,873,862 A 2/1999 Lopez
5,882,348 A 3/1999 Winterton et al.
5,899,888 A 5/1999 Jepson et al.
5,901,942 A 5/1999 Lopez
5,911,710 A 6/1999 Barry et al.
5,928,204 A 7/1999 Lopez
5,935,620 A 8/1999 Baudin
5,947,954 A 9/1999 Bonaldo
5,954,313 A 9/1999 Ryan
5,957,898 A 9/1999 Jepson et al.
5,967,490 A 10/1999 Pike
5,979,868 A 11/1999 Wu et al.
6,009,902 A 1/2000 Troiani et al.
6,019,748 A 2/2000 Lopez
6,029,946 A 2/2000 Doyle
6,036,171 A 3/2000 Weinheimer et al.
6,039,302 A 3/2000 Cote, Sr. et al.
6,048,335 A 4/2000 Mayer
6,050,978 A 4/2000 Orr et al.
6,063,062 A 5/2000 Paradis
6,079,432 A 6/2000 Paradis
6,089,541 A 7/2000 Weinheier et al.
6,099,511 A 8/2000 Devos et al.
6,113,068 A 9/2000 Ryan
6,116,571 A 9/2000 Hettinger
6,117,114 A 9/2000 Paradis
6,132,403 A 10/2000 Lopez
6,132,404 A 10/2000 Lopez
6,142,446 A 11/2000 Leinsing
6,152,900 A 11/2000 Mayer
6,162,206 A 12/2000 Bindokas et al.
6,162,251 A 12/2000 Kredovski
6,168,137 B1 1/2001 Paradis
6,170,800 B1 1/2001 Meloul et al.
6,171,287 B1 1/2001 Lynn
6,177,037 B1 1/2001 Mayer
6,183,448 B1 2/2001 Mayer
6,189,859 B1 2/2001 Rohrbough et al.
D438,955 S 3/2001 Rudzena
6,206,861 B1 3/2001 Mayer
6,210,624 B1 4/2001 Mayer
6,213,996 B1 4/2001 Jepson et al.
6,228,065 B1 5/2001 Lynn
6,228,069 B1 5/2001 Barth et al.
6,245,048 B1 6/2001 Fangrow et al.
6,254,579 B1 7/2001 Cogger et al.
6,261,282 B1 7/2001 Jepson et al.
6,261,630 B1 7/2001 Nazarova et al.
6,279,783 B1 8/2001 Brown et al.
6,290,206 B1 9/2001 Doyle
6,299,131 B1 10/2001 Ryan
6,299,132 B1 10/2001 Wienheimer
6,325,782 B1 12/2001 Lopez
D454,637 S 3/2002 Netenborg
6,364,861 B1 4/2002 Feith et al.
6,364,869 B1 4/2002 Bonaldo
6,390,130 B1 5/2002 Guala
6,428,520 B1 8/2002 Lopez et al.
6,444,324 B1 9/2002 Yang et al.
6,482,188 B1 11/2002 Rogers et al.
D468,015 S 12/2002 Horppu
D468,016 S 12/2002 Mosler et al.
6,541,802 B2 4/2003 Doyle
6,543,745 B1 4/2003 Enerson
D475,795 S 6/2003 Johnson et al.
6,572,592 B1 6/2003 Lopez
6,585,229 B2 7/2003 Cote, Sr. et al.
6,595,964 B2 7/2003 Finley et al.
6,595,981 B2 7/2003 Huet
6,599,273 B1 7/2003 Lopez
6,605,076 B1 8/2003 Jepson et al.
6,609,696 B2 8/2003 Enerson
6,635,044 B2 10/2003 Lopez
6,651,956 B2 11/2003 Miller
6,656,517 B2 12/2003 Michal et al.
6,669,673 B2 12/2003 Lopez
6,669,681 B2 12/2003 Jepson et al.
6,673,053 B2 1/2004 Wang et al.
6,682,509 B2 1/2004 Lopez
6,689,109 B2 2/2004 Lynn
6,695,817 B1 2/2004 Fangrow, Jr.
6,706,022 B1 3/2004 Leinsing et al.
6,712,791 B2 3/2004 Lui et al.
6,727,294 B2 4/2004 Kanayama et al.
6,740,063 B2 5/2004 Lynn
6,745,998 B2 6/2004 Doyle
6,755,391 B2 6/2004 Newton et al.
6,758,833 B2 7/2004 Lopez
6,783,709 B2 8/2004 Harreld et al.
6,802,490 B2 10/2004 Leinsing
6,808,161 B1 10/2004 Hishikawa
6,840,501 B2 1/2005 Doyle
6,848,139 B2 2/2005 Simon et al.
6,866,656 B2 3/2005 Tingey et al.
6,869,426 B2 3/2005 Ganem
6,871,838 B2 3/2005 Raines et al.
6,883,778 B1 4/2005 Newton et al.
6,892,998 B2 5/2005 Newton
6,908,459 B2 6/2005 Harding et al.

(56) References Cited

U.S. PATENT DOCUMENTS 6,916,309 B2 7/2005 Fangrow, Jr.
6,932,795 B2 8/2005 Lopez et al.
6,964,406 B2 11/2005 Doyle
6,991,215 B2 1/2006 Kiehne
6,994,315 B2 2/2006 Ryan et al.
6,997,917 B2 2/2006 Niedospial, Jr. et al.
7,014,169 B2 3/2006 Newton et al.
7,025,744 B2 4/2006 Utterberg et al.
7,033,339 B1 4/2006 Lynn
7,037,302 B2 5/2006 Vaillancourt
7,044,441 B2 5/2006 Doyle
7,074,216 B2 7/2006 Fowles et al.
7,100,890 B2 9/2006 Cote et al.
7,104,520 B2 9/2006 Leinsing et al.
7,114,701 B2 10/2006 Peppel
7,125,396 B2 10/2006 Leinsing et al.
7,140,592 B2 11/2006 Phillips et al.
7,184,825 B2 2/2007 Leinsing et al.
D546,946 S 7/2007 Blake
7,244,249 B2 7/2007 Leinsing et al.
7,252,652 B2 8/2007 Moorehead et al.
7,264,859 B2 9/2007 Souns et al.
D557,281 S 12/2007 Miller et al.
D557,283 S 12/2007 Miller et al.
7,306,197 B2 12/2007 Parrino et al.
7,306,199 B2 12/2007 Leinsing et al.
7,314,061 B2 1/2008 Peppel
7,326,188 B1 2/2008 Russell et al.
7,329,249 B2 2/2008 Bonaldo
7,335,182 B1 2/2008 Hilaire
7,357,792 B2 4/2008 Newton et al.
7,396,348 B2 7/2008 Newton et al.
7,422,369 B2 9/2008 Bergman et al.
D570,880 S 10/2008 Miller et al.
7,470,261 B2 12/2008 Lynn
7,470,262 B2 12/2008 Hiejima et al.
7,497,848 B2 3/2009 Leinsing et al.
7,497,849 B2 3/2009 Fangrow, Jr.
7,510,545 B2 3/2009 Peppel
7,520,489 B2 4/2009 Rushke
7,530,546 B2 5/2009 Ryan et al.
7,533,696 B2 5/2009 Paul, Jr.
7,556,060 B2 7/2009 Guala
7,559,530 B2 7/2009 Korogi et al.
7,563,243 B2 7/2009 Mendels
7,581,561 B2 9/2009 Funamura et al.
7,584,767 B2 9/2009 Funamura et al.
7,588,563 B2 9/2009 Guala
7,591,449 B2 9/2009 Raines et al.
7,601,141 B2 10/2009 Dikeman et al.
7,615,035 B2 11/2009 Peppel
7,624,749 B2 12/2009 Guala
7,628,774 B2 12/2009 Fangrow, Jr.
7,645,274 B2 1/2010 Whitley
7,651,481 B2 1/2010 Raybuck
7,666,170 B2 2/2010 Guala
7,673,653 B2 3/2010 Mijers et al.
7,703,486 B2 4/2010 Costanzo
7,713,250 B2 5/2010 Harding et al.
7,717,882 B2 5/2010 Harding
7,717,886 B2 5/2010 Lopez
7,743,799 B2 6/2010 Mosler et al.
7,753,338 B2 7/2010 Desecki
7,753,892 B2 7/2010 Newton et al.
7,758,566 B2 7/2010 Simpson et al.
7,763,013 B2 7/2010 Baldwin et al.
7,763,199 B2 7/2010 Fangrow
7,771,383 B2 8/2010 Truitt et al.
7,784,766 B2 8/2010 Guala
7,815,168 B2 10/2010 Vangsness et al.
7,824,393 B2 11/2010 Fangrow, Jr.
7,837,658 B2 11/2010 Cote, Sr. et al.
7,841,581 B2 11/2010 Thorne, Jr. et al.
7,842,026 B2 11/2010 Cahill et al.
7,857,284 B2 12/2010 Kimball et al.
7,857,285 B2 12/2010 Lee et al.
7,857,802 B2 12/2010 Brandenburger et al.
7,857,805 B2 12/2010 Raines
7,862,537 B2 1/2011 Zinger et al.
7,867,204 B2 1/2011 Bartholomew et al.
7,879,012 B2 2/2011 Kane et al.
7,900,659 B2 3/2011 Whitley et al.
7,905,873 B2 3/2011 Rondeau et al.
7,909,056 B2 3/2011 Truitt et al.
7,914,502 B2 3/2011 Newton et al.
D638,933 S 5/2011 Hill
7,947,032 B2 5/2011 Harding et al.
7,954,515 B2 6/2011 Gerst
7,975,722 B2 7/2011 Kiehne
7,981,090 B2 7/2011 Plishka et al.
7,981,381 B2 7/2011 Lurvey et al.
7,984,730 B2 7/2011 Ziv et al.
D643,920 S 8/2011 Gil Pascual
7,988,128 B2 8/2011 Wentling
7,993,328 B2 8/2011 Whitley
7,998,134 B2 8/2011 Fangrow
8,006,953 B2 8/2011 Bennett
D644,731 S 9/2011 Fangrow, Jr.
8,015,990 B2 9/2011 Pascal et al.
8,021,354 B2 9/2011 Huang
8,034,021 B2 10/2011 Mendels
8,034,035 B2 10/2011 Weaver et al.
8,038,663 B2 10/2011 Miner
8,042,838 B2 10/2011 Buckler et al.
8,048,038 B2 11/2011 Guala
8,062,266 B2 11/2011 McKinnon et al.
8,062,267 B2 11/2011 McKinnon et al.
8,062,280 B2 11/2011 Jepson et al.
8,066,648 B1 11/2011 Mark
8,066,669 B2 11/2011 Christensen et al.
8,066,670 B2 11/2011 Cluff et al.
8,070,189 B2 12/2011 Yow et al.
8,070,725 B2 12/2011 Christensen
8,074,964 B2 12/2011 Mansour et al.
8,096,525 B2 1/2012 Ryan
8,100,868 B2 1/2012 Newton et al.
8,100,869 B2 1/2012 Vangsness et al.
8,105,314 B2 1/2012 Fangrow
D654,166 S 2/2012 Lair
D655,000 S 2/2012 Mirigian
8,123,738 B2 2/2012 Vaillancourt
8,133,209 B2 3/2012 Guala
8,136,330 B2 3/2012 Ostler et al.
8,137,303 B2 3/2012 Stout et al.
8,142,403 B2 3/2012 Carlyon
8,152,790 B2 4/2012 Lopez et al.
8,156,971 B2 4/2012 Costanzo
8,162,006 B2 4/2012 Guala
8,162,013 B2 4/2012 Rosenquist et al.
8,162,914 B2 4/2012 Kraushaar et al.
8,167,863 B2 5/2012 Yow
8,172,823 B2 5/2012 Rondeau et al.
8,177,760 B2 5/2012 Rome et al.
8,177,768 B2 5/2012 Leinsing
8,177,772 B2 5/2012 Christensen et al.
8,182,452 B2 5/2012 Mansourt et al.
8,197,452 B2 6/2012 Harding et al.
8,197,466 B2 6/2012 Yokota et al.
8,211,089 B2 7/2012 Winsor et al.
8,221,363 B2 7/2012 Jepson
8,221,391 B2 7/2012 Fangrow, Jr.
8,241,268 B2 8/2012 Whitley
8,277,424 B2 10/2012 Pan
8,286,657 B2 10/2012 Belley et al.
8,286,936 B2 10/2012 Kitani et al.
8,287,518 B2 10/2012 Kitani et al.
8,298,195 B2 10/2012 Peppel
8,298,196 B1 10/2012 Mansour
8,337,483 B2 12/2012 Harding et al.
8,361,408 B2 1/2013 Lynn
8,366,658 B2 2/2013 Davis et al.
8,366,676 B2 2/2013 Harding et al.
8,372,043 B2 2/2013 Grimm et al.
8,377,010 B2 2/2013 Harding et al.

(56) References Cited

U.S. PATENT DOCUMENTS 8,382,741 B2 2/2013 Chelak
8,398,598 B2 3/2013 Carlyon et al.
8,398,607 B2 3/2013 Fangrow, Jr.
8,403,886 B2 3/2013 Bialecki et al.
8,403,894 B2 3/2013 Lynn et al.
8,403,905 B2 3/2013 Yow
8,408,226 B2 4/2013 Raines et al.
8,409,164 B2 4/2013 Fangrow
8,409,165 B2 4/2013 Niedospial, Jr. et al.
8,414,542 B2 4/2013 Stroup
8,439,880 B2 5/2013 Rondeau
8,444,628 B2 5/2013 Fangrow, Jr.
8,454,579 B2 6/2013 Fangrow, Jr.
8,529,524 B2 9/2013 Newton et al.
8,628,515 B2 1/2014 Fangrow, Jr. et al.
8,636,720 B2 1/2014 Truitt et al.
8,640,725 B2 2/2014 Truitt et al.
8,671,964 B2 3/2014 Py
8,679,090 B2 3/2014 Anderson et al.
8,684,994 B2 4/2014 Lev et al.
8,701,696 B2 4/2014 Guala
8,702,675 B2 4/2014 Imai
8,715,222 B2 5/2014 Truitt et al.
8,715,247 B2 5/2014 Mansour et al.
8,721,627 B2 5/2014 Albert
D707,355 S 6/2014 Bow
8,747,370 B2 6/2014 Feith et al.
8,758,306 B2 6/2014 Lopez et al.
8,801,678 B2 8/2014 Panian et al.
8,834,432 B2 9/2014 Winsor et al.
8,840,577 B1 9/2014 Zollinger et al.
8,864,725 B2 10/2014 Ranalletta et al.
8,870,846 B2 10/2014 Davis et al.
8,876,784 B2 11/2014 Cote, Sr. et al.
8,882,742 B2 11/2014 Dikeman et al.
8,910,919 B2 12/2014 Bonnal et al.
8,951,233 B2 2/2015 Mansour
8,968,261 B2 3/2015 Kimball et al.
8,968,271 B2 3/2015 Guala
8,974,425 B2 3/2015 Tachizaki et al.
8,979,804 B2 3/2015 Ho et al.
9,017,295 B2 4/2015 Pan
9,032,997 B2 5/2015 Abura et al.
9,039,047 B2 5/2015 Imai
9,044,585 B2 6/2015 Masuda et al.
9,061,130 B2 6/2015 Truitt et al.
9,067,049 B2 6/2015 Panian et al.
D734,456 S 7/2015 Cromett
9,089,680 B2 7/2015 Ueda et al.
9,089,681 B2 7/2015 Ueda et al.
9,089,682 B2 7/2015 Yeh et al.
D737,436 S 8/2015 Lev
9,108,034 B2 8/2015 Winsor
9,114,244 B2 8/2015 Yeh et al.
9,119,950 B2 9/2015 Mansour et al.
9,138,572 B2 9/2015 Zeytoonian et al.
9,144,672 B2 9/2015 Mansour et al.
9,162,029 B2 10/2015 Zollinger
9,192,753 B2 11/2015 Lopez et al.
9,198,831 B2 12/2015 Rogers
9,205,243 B2 12/2015 Lopez et al.
9,212,772 B2 12/2015 Ho et al.
9,220,882 B2 12/2015 Belley et al.
9,234,616 B2 1/2016 Carrez et al.
9,238,128 B2 1/2016 Yamaguchi et al.
9,278,205 B2 3/2016 Quach et al.
9,278,206 B2 3/2016 Fangrow et al.
9,289,588 B2 3/2016 Chen
D753,283 S 4/2016 Efinger
9,314,604 B2 4/2016 Bonnal et al.
9,345,641 B2 5/2016 Krause et al.
9,352,086 B2 5/2016 Guala
9,370,466 B2 6/2016 Garfield et al.
9,370,651 B2 6/2016 Zollinger et al.
9,375,559 B2 6/2016 Feith et al.
9,381,339 B2 7/2016 Wu et al.
9,393,398 B2 7/2016 Truitt et al.
9,409,007 B2 8/2016 Yeh
9,421,354 B2 8/2016 Carmody et al.
9,433,708 B2 9/2016 Eddy
D786,427 S 5/2017 Nelson
D793,551 S 8/2017 Nelson
2001/0049508 A1 12/2001 Fangrow, Jr.
2002/0120333 A1 8/2002 Keogh et al.
2004/0006330 A1 1/2004 Fangrow, Jr.
2005/0020981 A1 1/2005 Kurth
2005/0059952 A1 3/2005 Giuliano et al.
2005/0121638 A1 6/2005 Doyle
2005/0222541 A1 10/2005 Lopez et al.
2006/0004331 A1 1/2006 Fangrow, Jr.
2006/0161115 A1 7/2006 Fangrow, Jr.
2006/0200088 A1 9/2006 Lopez
2006/0200089 A1 9/2006 Lopez et al.
2006/0200090 A1 9/2006 Lopez et al.
2006/0206061 A1 9/2006 Lopez et al.
2006/0211997 A1 9/2006 Fangrow, Jr.
2006/0211998 A1 9/2006 Fangrow, Jr.
2006/0211999 A1 9/2006 Fangrow, Jr.
2006/0212001 A1 9/2006 Fangrow, Jr.
2006/0212003 A1 9/2006 Fangrow, Jr.
2006/0212006 A1 9/2006 Fangrow, Jr.
2006/0224127 A1 10/2006 Fangrow, Jr.
2006/0264842 A1 11/2006 Fangrow, Jr.
2006/0264844 A1 11/2006 Fangrow, Jr.
2006/0264849 A1 11/2006 Lopez et al.
2006/0264909 A1 11/2006 Fangrow, Jr.
2006/0264910 A1 11/2006 Fangrow, Jr.
2006/0270999 A1 11/2006 Fangrow, Jr.
2006/0271016 A1 11/2006 Fangrow, Jr.
2006/0276757 A1 12/2006 Fangrow, Jr.
2006/0276758 A1 12/2006 Fangrow, Jr.
2007/0100284 A1 5/2007 Leinsing et al.
2007/0106205 A1 5/2007 Connell et al.
2007/0112312 A1 5/2007 Fangrow, Jr.
2007/0112313 A1 5/2007 Fangrow, Jr.
2007/0224865 A1 9/2007 Fangrow, Jr.
2007/0225425 A1 9/2007 Nash et al.
2007/0235676 A1 10/2007 Vangsness et al.
2007/0254000 A1 11/2007 Guo et al.
2007/0270756 A1 11/2007 Peppel et al.
2008/0039802 A1 2/2008 Vangsness et al.
2008/0086097 A1 4/2008 Rasmussen et al.
2008/0086099 A1 4/2008 McKinnon et al.
2008/0097407 A1 4/2008 Plishka
2008/0249508 A1 10/2008 Lopez et al.
2009/0005761 A1 1/2009 Guala
2009/0087606 A1* 4/2009 Julien ...................... B32B 1/08
428/36.7
2009/0198209 A1 8/2009 Usher et al.
2009/0209922 A1 8/2009 Boisjoly
2009/0292252 A1 11/2009 Lareau et al.
2010/0030163 A1 2/2010 Carrez et al.
2010/0030164 A1 2/2010 Kimball et al.
2010/0036330 A1 2/2010 Plishka et al.
2010/0059474 A1 3/2010 Brandenburger et al.
2010/0059702 A1 3/2010 Mansour et al.
2010/0063456 A1 3/2010 Rahimy et al.
2010/0063482 A1 3/2010 Mansour
2010/0108681 A1 5/2010 Jepson et al.
2010/0152680 A1 6/2010 Memahon
2010/0174242 A1 7/2010 Anderson et al.
2010/0241088 A1 9/2010 Ranalletta et al.
2010/0249723 A1 9/2010 Fangrow, Jr.
2010/0249724 A1 9/2010 Cote, Sr. et al.
2010/0249725 A1 9/2010 Cote, Sr. et al.
2010/0264343 A1 10/2010 Jeory
2010/0270792 A1 10/2010 Lauer
2010/0283238 A1 11/2010 Deighan et al.
2010/0292673 A1 11/2010 Korogi et al.
2010/0292674 A1 11/2010 Jepson et al.
2010/0300556 A1 12/2010 Carmody et al.
2010/0324502 A1 12/2010 Guala
2011/0004183 A1 1/2011 Carrez et al.
2011/0024664 A1 2/2011 Burnard et al.

(56) References Cited

U.S. PATENT DOCUMENTS

2011/0028914 A1 2/2011 Mansour et al.
2011/0028915 A1 2/2011 Siopes et al.
2011/0046572 A1 2/2011 Fangrow
2011/0048540 A1 3/2011 Stroup
2011/0054440 A1 3/2011 Lewis
2011/0060293 A1 3/2011 Guala
2011/0087164 A1 4/2011 Mosler et al.
2011/0106046 A1 5/2011 Hiranuma et al.
2011/0125104 A1 5/2011 Lynn
2011/0130717 A1 6/2011 David et al.
2011/0130724 A1 6/2011 Mansour et al.
2011/0130726 A1 6/2011 Crawford et al.
2011/0130727 A1 6/2011 Crawford et al.
2011/0130728 A1 6/2011 McKinnon
2011/0152832 A1 6/2011 Foshee et al.
2011/0166532 A1 7/2011 Brandenburger et al.
2011/0178493 A1 7/2011 Okiyama
2011/0257590 A1 10/2011 Winsor et al.
2011/0264037 A1 10/2011 Foshee et al.
2011/0266477 A1 11/2011 Stroup
2011/0275988 A1 11/2011 Davis et al.
2011/0276010 A1 11/2011 Davis et al.
2011/0276031 A1 11/2011 Hoang et al.
2011/0295235 A1 12/2011 Fangrow
2011/0306940 A1 12/2011 Miyasaka
2011/0319821 A1 12/2011 Kitani et al.
2011/0319859 A1 12/2011 Zeytoonian et al.
2012/0013121 A1 1/2012 Weckstrom
2012/0022469 A1 1/2012 Alpert
2012/0042971 A1 2/2012 Py
2012/0046636 A1 2/2012 Kriheli
2012/0053529 A1 3/2012 Imai
2012/0059314 A1 3/2012 Eichhorst
2012/0059334 A1 3/2012 Pan
2012/0059346 A1 3/2012 Sheppard et al.
2012/0065626 A1 3/2012 Naftalovitz et al.
2012/0095407 A1 4/2012 Chebator et al.
2012/0109077 A1 5/2012 Ryan
2012/0130305 A1 5/2012 Bonnal et al.
2012/0130352 A1 5/2012 Naftalovitz et al.
2012/0150129 A1 6/2012 Jin et al.
2012/0153201 A1 6/2012 Larose et al.
2012/0157928 A1 6/2012 Mermet
2012/0157933 A1 6/2012 Newton et al.
2012/0179108 A1 7/2012 Delabie
2012/0192968 A1 8/2012 Bonnal et al.
2012/0209238 A1 8/2012 Rosenquist et al.
2012/0215182 A1 8/2012 Mansour et al.
2012/0220955 A1 8/2012 Maseda et al.
2012/0220977 A1 8/2012 Yow
2012/0220984 A1 8/2012 Christensen et al.
2012/0245564 A1 9/2012 Tekeste et al.
2012/0259292 A1 10/2012 Koehler
2012/0316514 A1 12/2012 Mansour
2012/0316536 A1 12/2012 Carrez et al.
2012/0323063 A1 12/2012 Costanzo
2012/0330277 A1 12/2012 Winsor et al.
2013/0012870 A1 1/2013 Dikeman et al.
2013/0030386 A1 1/2013 Panian et al.
2013/0035668 A1 2/2013 Kitani et al.
2013/0046315 A1 2/2013 Woehr et al.
2013/0053815 A1 2/2013 Mucientes et al.
2013/0060205 A1 3/2013 Mansour et al.
2013/0066293 A1 3/2013 Garfield et al.
2013/0079730 A1 3/2013 Mosler et al.
2013/0138075 A1 5/2013 Lambert
2013/0253478 A1 9/2013 Fangrow, Jr.
2013/0289534 A1 10/2013 Fangrow, Jr.
2013/0331800 A1 12/2013 Newton et al.
2014/0031765 A1 1/2014 Siopes et al.
2014/0135709 A1 5/2014 Zollinger
2014/0142519 A1 5/2014 Truitt et al.
2014/0155836 A1 6/2014 Truitt et al.
2014/0174578 A1 6/2014 Bonnal et al.
2014/0180219 A1 6/2014 Ho et al.
2014/0180258 A1 6/2014 Ho et al.
2014/0209197 A1 7/2014 Carrez et al.
2014/0257198 A1 9/2014 Truitt et al.
2014/0261860 A1 9/2014 Heath et al.
2014/0276455 A1 9/2014 Yeh et al.
2014/0276456 A1 9/2014 Eddy
2014/0276458 A1 9/2014 Mansour et al.
2014/0276459 A1 9/2014 Yeh et al.
2014/0276463 A1 9/2014 Mansour et al.
2014/0276466 A1 9/2014 Yeh et al.
2014/0296794 A1 10/2014 Li
2014/0303602 A1 10/2014 Mansour et al.
2014/0316350 A1 10/2014 Yamaguchi et al.
2014/0358033 A1 12/2014 Lynn
2014/0371686 A1 12/2014 Sano et al.
2015/0040987 A1 2/2015 Reichert et al.
2015/0040988 A1 2/2015 Reichert et al.
2015/0045746 A1 2/2015 Macy, Jr. et al.
2015/0045772 A1 2/2015 Reichert et al.
2015/0126942 A1 5/2015 Lopez et al.
2015/0148756 A1 5/2015 Lynn
2015/0151100 A1 6/2015 Mansour
2015/0157799 A1 6/2015 Chen et al.
2015/0157800 A1 6/2015 Chen et al.
2015/0157848 A1 6/2015 Wu et al.
2015/0176715 A1 6/2015 Huang et al.
2015/0190627 A1 7/2015 Ueda et al.
2015/0196749 A1 7/2015 Ziv et al.
2015/0196750 A1 7/2015 Ueda et al.
2015/0202424 A1 7/2015 Harton
2015/0258325 A1 9/2015 Panian et al.
2015/0265827 A1 9/2015 Keyser et al.
2015/0265829 A1 9/2015 Truitt et al.
2015/0297817 A1 10/2015 Guala
2015/0297880 A1 10/2015 Ogawa et al.
2015/0313523 A1 11/2015 Chelak et al.
2015/0374910 A1 12/2015 Mansour
2016/0000364 A1 1/2016 Mendels et al.
2016/0001057 A1 1/2016 Lopez et al.
2016/0015958 A1 1/2016 Ueda et al.
2016/0015960 A1 1/2016 Bonnal
2016/0015961 A1 1/2016 Mansour et al.
2016/0022977 A1 1/2016 Ueda et al.
2016/0022978 A1 1/2016 Ueda
2016/0030730 A1 2/2016 Mosler et al.
2016/0038730 A1 2/2016 Zollinger
2016/0089492 A1 3/2016 Burnard et al.
2016/0089529 A1 3/2016 Bolz et al.
2016/0114147 A1 4/2016 Siopes et al.
2016/0129235 A1 5/2016 Ryan
2016/0136051 A1 5/2016 Lavi
2016/0144110 A1 5/2016 Ueda
2016/0158524 A1 6/2016 Quach et al.
2016/0235961 A1 8/2016 Maffei
2016/0317798 A1 11/2016 Lopez et al.

FOREIGN PATENT DOCUMENTS

CA 2 175 021 11/1996
CH 636526 6/1983
CH 670955 7/1989
DE 855 319 9/1952
DE 84 25 197.2 9/1985
DE 37 40 269 6/1989
EP 0 263 789 4/1988
EP 0 309 771 4/1989
EP 0 399 119 11/1990
EP 0 446 463 9/1991
GB 2 000 685 1/1979
GB 2 001 146 1/1979
GB 2 034 185 6/1980
WO WO 1992/20736 11/1992
WO WO 1999/59672 11/1999
WO WO 1999/61093 12/1999
WO WO 2003/018104 3/2003
WO WO 2005/115521 8/2005
WO WO 2006/013433 2/2006
WO WO 2006/062912 6/2006
WO WO 2008/048777 4/2008

(56) References Cited

FOREIGN PATENT DOCUMENTS

| | | |
|---|---|---|
| WO | WO 2009/052433 | 4/2009 |
| WO | WO 2009/111596 | 9/2009 |
| WO | WO 2010/004471 | 1/2010 |

OTHER PUBLICATIONS

U.S. Appl. No. 29/510,852, filed Dec. 3, 2014, Nelson.
U.S. Appl. No. 14/961,163, filed Dec. 7, 2015, Lopez et al.
"Faulding Inc. receives FDA permission to market patented Safe-Connect Valve", dated Dec. 2, 1996.
BD Medical: Needleless IV Access Devices, one page, 2007.
Capless Backcheck Valve, dated Sep. 3, 1993, in 2 pages.
CardinalHealth, SmartSite Brochure: "SmartSite® Disposables," 2004, in 12 pages.
CareFusion, Medegen Introduces MaxPlus® Clear, First and Only Clear Positive Displacement Connector for Use in Infusion Therapy, MaxGuard News, one page article, dated Mar. 10, 2008—Ontario, CA.
Caresite™ Luer Access Device, dated 2010, in 2 pages.
Clearlink, needleless IV access system, Baxter 2007 brochure, in 2 pages.
F.D.A. 510(k) Summary of Safety and Effectiveness, dated Nov. 17, 1997, in 5 pages.
LifeShield TKO Anti-Reflux Device Brochure, appears to contain a date of Feb. 8, in 8 pages.
MEDI-4955 Liquid Silicone Rubber from NuSil Silicone Technology, dated Dec. 17, 2010, in 2 pages.
MicroClave Connector Brochure. The MicroClave was available before Mar. 25, 2008, in 2 pages.
MicroClave Neutral Displacement Connector A Neddlefree Closed System Device. Brochure Sep. 24, 2008, in 2 pages.
MicroClave Product Page Video Shots. Sep. 24, 2008, in 2 pages.
Nexus Medical Nexus TKO, appears to contain a date of Mar. 2006, in 6 pages.
PASV Valve Connector Brochure, which appears to be at least as early as Feb. 20, 2001, in 2 pages.
Saechtling Tworzywa Sztuczne, (with English translation) WN-T Warszawa, 1999, V edition, pp. 224-225.
U.S. Appl. No. 29/603,008, filed May 5, 2017, Nelson.
U.S. Appl. No. 29/611,987, filed Jul. 27, 2017, Nelson.

* cited by examiner 22
20
50
10
60
40
42
14
80
70
100
30
32
34

22
20
50'
50'
60'
14
40'
70'
80'
50'
50'
60'
42'
50'
50'
10'
30
32
34

100
120
R4
R5
2
110
120

100
$t_1$
$h_1$
120
110
$w_1$
$w_2$
$w_1$
120

100
110
120
114
112
122
120

100
120
110
114
116
122
120

MEDICAL FLUID MANIFOLD

RELATED APPLICATIONS

This application is a continuation of PCT/US2014/068455, filed Dec. 3, 2014, titled CHECK VALVE, which claims the benefit of U.S. Provisional Application No. 61/914,892, filed Dec. 11, 2013, titled CHECK VALVE, the entire contents of each are incorporated by reference herein and made a part of this specification.

BACKGROUND

1. Field of the Disclosure

A variety of devices and techniques exist for the manipulation of fluids in hospitals and medical settings, and in particular the selective facilitation of fluid movement to or from patients or to or from a fluid flow line. Fluid flow lines rely on a variety of connectors to help develop preferred flow characteristics or access points. Many connectors include check valves.

2. Description of the Related Art

Current fluid flow systems, medical connectors, and check valves have various limitations and disadvantages and a need exists for further improvement.

SUMMARY OF THE DISCLOSURE

A variety of fluid flow lines and systems are used in hospitals and medical settings for the selective facilitation of fluid movement to or from patients. For example, central venous catheters can be used to administer IV fluids, various medications or blood products, and/or parenteral nutrition. In some embodiments, medical connectors can be provided on one end of a flow line to allow for periodic access to a flow line or for application of different inputs to the flow line. Generally, these structures require valves to allow fluid to enter the main flow line while preventing retrograde flow.

In certain situations, it may be desirable to provide multiple connections to a flow line into a patient's blood stream. This can allow for easy connection to multiple fluid or medication sources. This is particularly useful in treatments that require multiple inputs, such as chemotherapy. When multiple connections are desired, a manifold, extension set, or other multi-input structure can be used. These structures also require valves to allow fluid to enter the main flow line but that preferably prevent retrograde flow. In various embodiments described herein, such valves can be designed to maximize efficiency and desired flow rates and flow characteristics while still providing a check on retrograde flow. In some situations, it may be desirable to provide a single connection point with one way flow.

In various embodiments, a medical check valve for use in a medical device to provide one-way fluid flow between a first fluid location and a second fluid location can include a flexible diaphragm having a top surface, a bottom surface, and a side wall between the top surface and the bottom surface, and a first support member extending from the bottom surface of the flexible diaphragm and a second support member extending from the bottom surface of the flexible diaphragm, the first support member and second support member positioned to define a line of or axis of symmetry that bisects the bottom surface without passing through the first support member or the second support member. The flexible diaphragm can have a first position in which the top surface is generally planar and is configured to seal against a fluid opening and a second position in which the top surface of the diaphragm is curved generally around the line of symmetry and is configured to be displaced from the fluid opening.

In some embodiments, the line of symmetry can be the only line of symmetry that bisects the bottom surface without passing through the first support member or the second support member. In some embodiments, the flexible diaphragm can be a disc. In some embodiments, the support members can be positioned 180 degrees apart about the disc. In some embodiments, the flexible diaphragm can be nonperforate. In some embodiments, the flexible diaphragm, the first support member, and the second support member can be integrally formed and/or molded into a single unitary piece.

In some embodiments, the diaphragm can be configured to move from the first position to the second position at varying amounts of pressure. For example, in some embodiments a net pressure of less than 3 psi on the top surface of the flexible diaphragm is sufficient to move the diaphragm from the first position to the second position. In some embodiments, a net pressure of less than 1 psi on the top surface of the flexible diaphragm is sufficient to move the diaphragm from the first position to the second position. In some embodiments, a positive net pressure on the bottom surface of the flexible diaphragm is needed to maintain the flexible diaphragm in the first position.

In various embodiments, a medical manifold for use in providing access to a fluid flow path can include a housing having a first port, a second port, a first channel connecting the first port and the second port and defining a first flow path, and a third port having a recess in an outer wall of the housing and a second channel fluidly connecting the recess and the first flow path. The manifold can also include a valve member having a diaphragm and a plurality of support members configured to be positioned in the recess to thereby define a space between a bottom wall of the recess and the diaphragm. The manifold can also include a medical connector configured to attach to the third port, wherein the valve member in a closed position is configured to seal against an opening into the medical connector and the valve member in an open position is configured to allow fluid to flow from the medical connector, past the valve member, through the second channel, and into the first flow path.

In some embodiments, an outer wall of the recess can be cylindrical. In some embodiments, an outer wall of the recess can include multiple walls. In some embodiments, the third port can have at least two projections extending from the bottom wall of the recess and adjacent the second channel, wherein the projections define an outer channel between the projections and an outer wall of the recess and at least two transverse channels between the projections. In some embodiments, the plurality of support members can be configured to be positioned on at least two of the projections. In such embodiments, the valve member in an open position is configured to allow fluid to flow from the medical connector, past the valve member to the outer channel, through the transverse channels, and into the second channel.

In some embodiments, the valve member can be biased toward the closed position. In some embodiments, the valve member can be configured to move from the closed to the open position as a result of pressure from fluid in the medical connector. In some embodiments, the housing can be monolithic. In some embodiments, a net pressure of less than 3 psi on the valve member can be sufficient to move the valve member from the closed position to the open position.

In various embodiments, a medical manifold for use in providing access to a fluid flow path can include a first port, a second port, a first channel connecting the first port and the second port and defining a first flow path, and a housing having a third port in an outer wall of the housing and a second channel fluidly connecting the third port and the first flow path. The manifold can also include a valve member having a diaphragm and a plurality of support members configured to be positioned in the third port to thereby define a space between a bottom wall of the third port and the diaphragm. The manifold can also include a medical connector configured to attach to the third port, wherein the valve member in a closed position is configured to seal against an opening into the medical connector and the valve member in an open position is configured to allow fluid to flow from the medical connector, past the valve member, through the second channel, and into the first flow path.

In some embodiments, the third port further includes at least two projections extending from the bottom wall of the third port and adjacent the second channel, wherein the projections define at least two transverse channels between the projections. The plurality of support members may be configured to be positioned on at least two of the projections. In some embodiments, the third port of the medical manifold includes a recess and the projections extend from the bottom wall of the recess. A wall surrounding the recess may extend outward from the housing and a portion of the medical connector may be configured to surround at least a portion of the wall. In some embodiments, the medical connector is sonically welded to the third port.

In some embodiments, an outer wall of the third port can be cylindrical. In some embodiments, an outer wall of the third port can include multiple walls. In some embodiments, the third port can have at least two projections extending from the bottom wall of the third port and adjacent the second channel, wherein the projections define an outer channel between the projections and an outer wall of the third port and at least two transverse channels between the projections. In some embodiments, the plurality of support members can be configured to be positioned on at least two of the projections. In such embodiments, the valve member in an open position is configured to allow fluid to flow from the medical connector, past the valve member to the outer channel, through the transverse channels, and into the second channel.

In various embodiments, a medical manifold for use in providing access to a fluid flow path can include a first port, a second port, a first channel connecting the first port and the second port and defining a first flow path, and a housing having a third port in an outer wall of the housing and a second channel fluidly connecting the third port and the first flow path. The manifold can also include a valve member having a diaphragm and a plurality of support members configured to be positioned in the third port to thereby define a space between a bottom wall of the third port and the diaphragm. The manifold can also include a medical connector configured to attach to the third port, wherein the valve member in a closed position is configured to seal against an opening into the medical connector and the valve member in an open position is configured to allow fluid to flow from the medical connector, past the valve member, through the second channel, and into the first flow path. The medical manifold can also include a second housing including a fourth port with a third channel fluidly connecting the fourth port and the first flow path. In some embodiments, the manifold can include a second valve member with a diaphragm and a plurality of support members configured to be positioned in the fourth port to thereby define a space between a bottom wall of the fourth port and the diaphragm. Some manifolds can include a second medical connector configured to attach to the fourth port, wherein the second valve member in a closed position is configured to seal against an opening into the second medical connector and the second valve member in an open position is configured to allow fluid to flow from the second medical connector, past the second valve member, through the third channel, and into the first flow path. In some embodiments, the first and second housings are monolithic while in other embodiments, wherein the first and second housings are joined by a flexible connecting element.

DETAILED DESCRIPTION OF THE PREFERRED EMBODIMENTS

With reference to the attached figures, certain embodiments and examples of fluid flow systems, medical connectors, and valves will now be described. Various embodiments of check valves described herein are with reference to a manifold or extension set, but they are not so limited. In some aspects, they can be applied to any system to provide for one-way flow between a medical connector and a fluid flow line, such as in, for example, IV sets, stopcocks or other branched connectors including y-site connectors, and other systems. As used herein, the term "fluid" refers to either gases or liquids.

Figure 1:
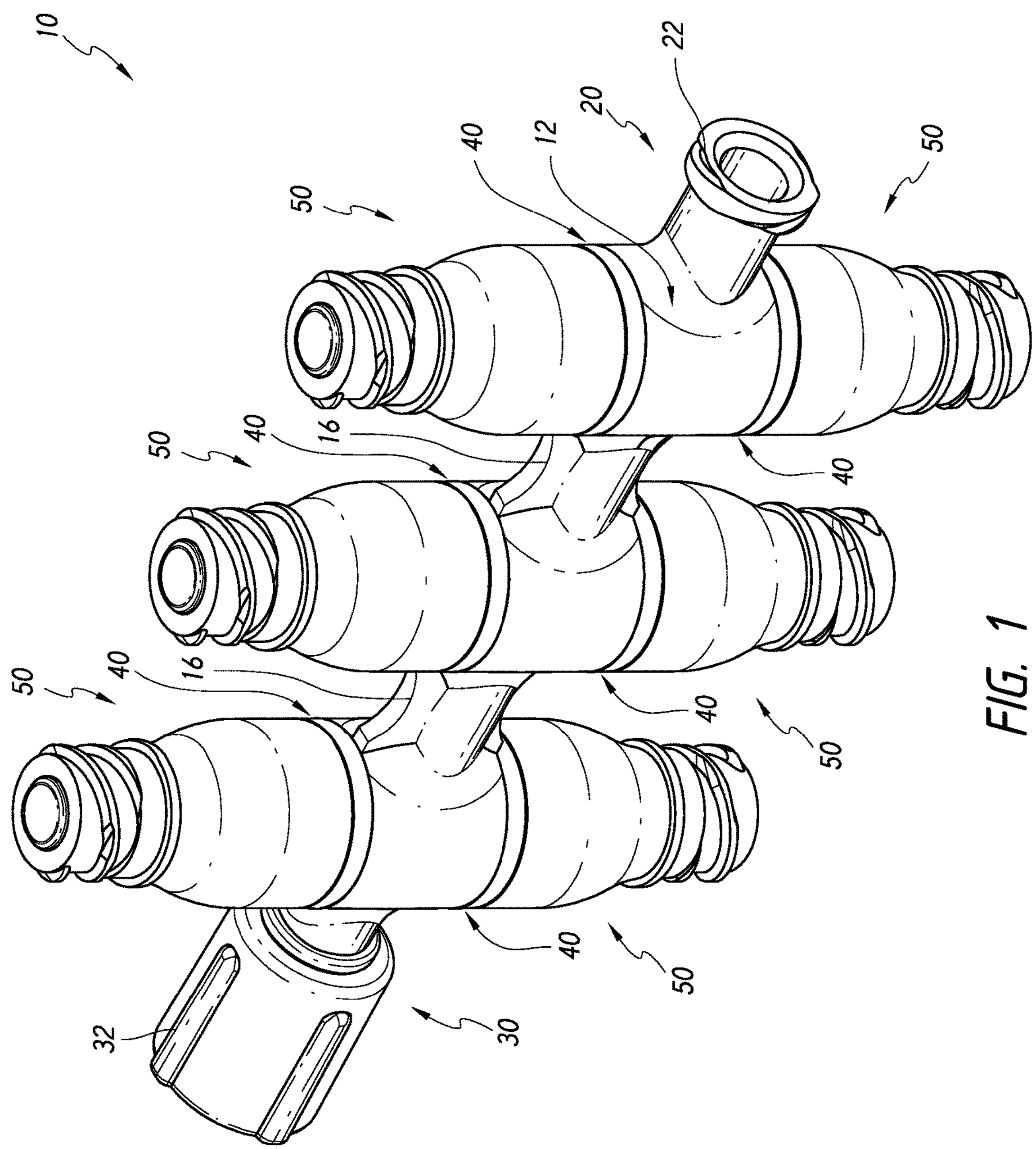
FIG. 1 is a perspective view of one embodiment of a manifold.

FIG. 1 illustrates an embodiment of a manifold 10 that can be used to provide access to a fluid flow path. The manifold can include a manifold housing 12 that can include a first port 20 and a second port 30. In some embodiments, the housing can be one integral piece, and in some embodiments it can include multiple pieces such that the manifold includes first and second ports connected by a fluid path, but the ports are connected by separately formed units, for example tubes, to the housing. In some embodiments, multiple housings may be connected between the first and second ports. Preferably, even when connected by flexible joints, the manifold in a resting position defines a generally linear fluid path between the first and second ports with one or more ports branching off that path. In some embodiments, those one or more ports branch off at about 90 degrees from the flow path between the first and second ports. The manifold can be inserted into a fluid flow line with the first port 20 configured to attach to one end of the line and the second port 30 configured to attach to a second end of the line. The ports can be configured to accommodate any standard medical connector or implement, and can be adapted to conform with ANSI (American National Standards Institute) or other applicable standards. In some embodiments, different ports can also be configured to have nonstandard connections.

In some embodiments, a first port 20 can have a threaded end 22 that can be used to connect to a threaded medical connector. In some embodiments, a second port 30 can have a male luer lock 32, including a tapered cannula 34 (visible in FIGS. 3 and 4).

In some embodiments, the manifold 10 can include a plurality of access ports 40, described and illustrated in more detail below. The access ports can be adapted to connect or attach to a variety of types of medical connectors 50. In some embodiments, as illustrated, a medical connector 50 can be a needleless connector. In the illustrated embodiment, the manifold includes six medical connectors 50, three on a first side of the manifold and three on a second side of the manifold.

Figure 2:
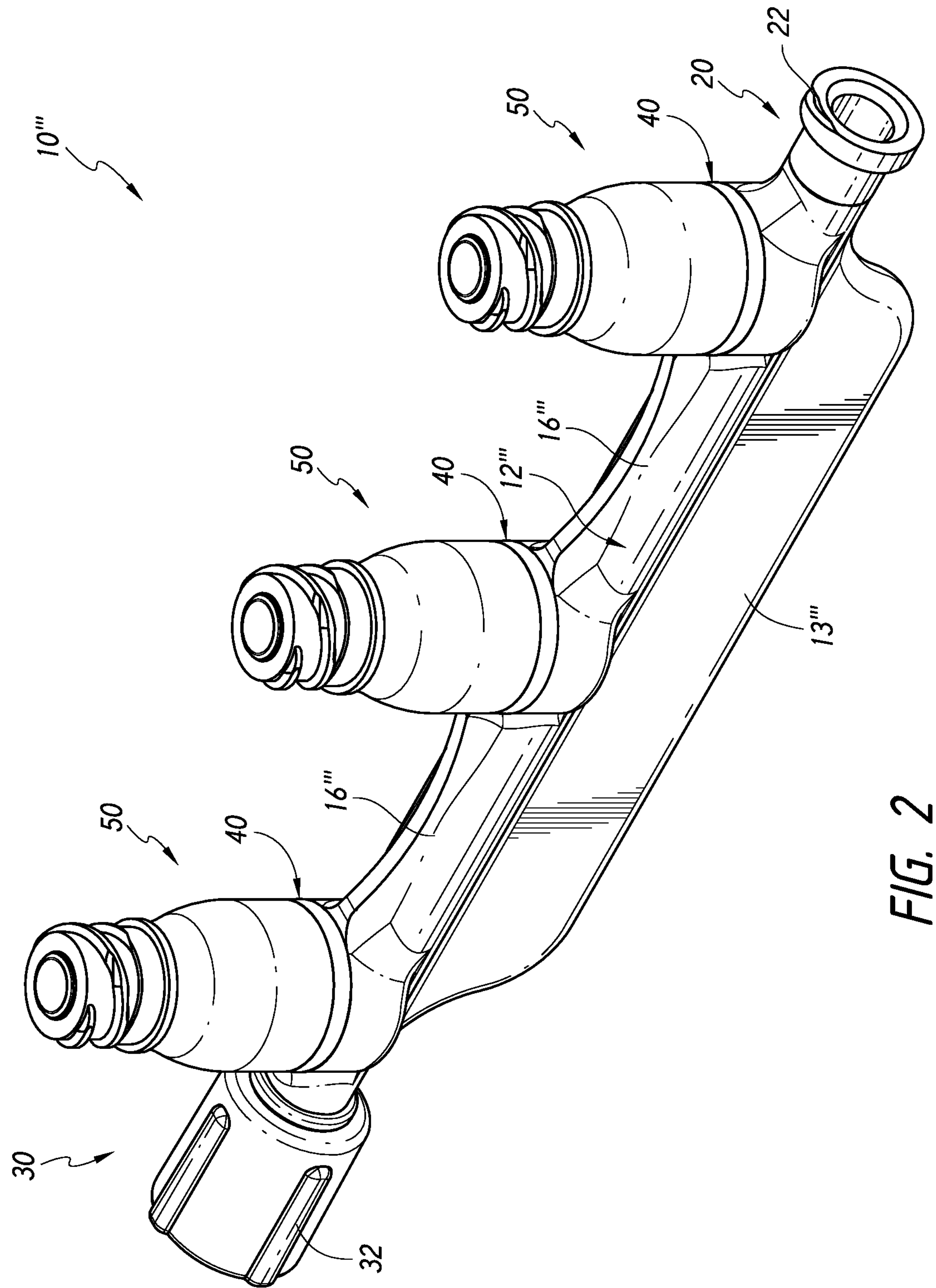
FIG. 2 is a perspective view of one embodiment of a manifold.
Figure 2A:
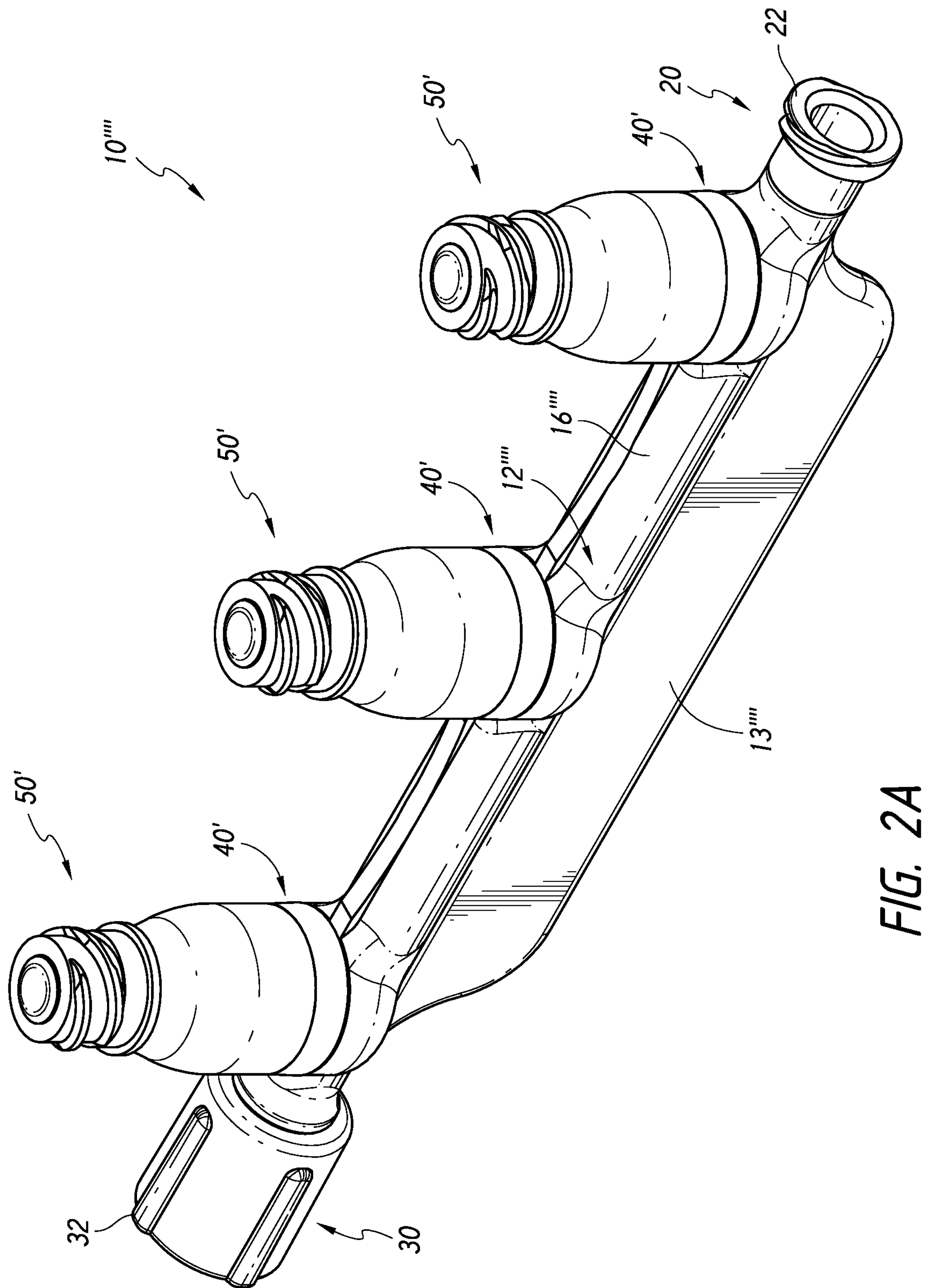
FIG. 2A is a perspective view of an embodiment of a manifold with a modified projection attachment.

In various embodiments, a manifold can have varying numbers of access ports and medical connectors. For example, FIG. 2 illustrates an embodiment of a manifold 10''' that has three access ports and medical connectors 50 on one side of the manifold. Housing 12''' includes joints 16''' and can include an extended portion or fin 13 that may be positioned on the side opposite the medical connectors. Fin 13''' can be provided to add stability to the manifold 10''' and may be configured to facilitate the handling or control by a nurse or other user of the manifold 10''' during use or to attach the manifold 10' to a convenient resting place. FIG. 2A shows an alternative manifold 10'''' also including three access ports and medical connectors 50' on one side. Housing 12'''' includes joints 16'''' and can include an extended portion or fin 13'''' that may be positioned on the side opposite the medical connectors. Fin 13'''' can be provided to add stability to the manifold 10'''' and may be configured to facilitate the handling or control by a nurse or other user of the manifold 10'''' during use or to attach the manifold 10'''' to a convenient resting place. As shown, joints 16'''' may include shallow curved portions as compared to the curved portions on joints 16''' shown in FIG. 2. Curved portions and other structures can be used to change the strength of the housing and to provide a convenient place to hold the manifold.

Figure 1A:
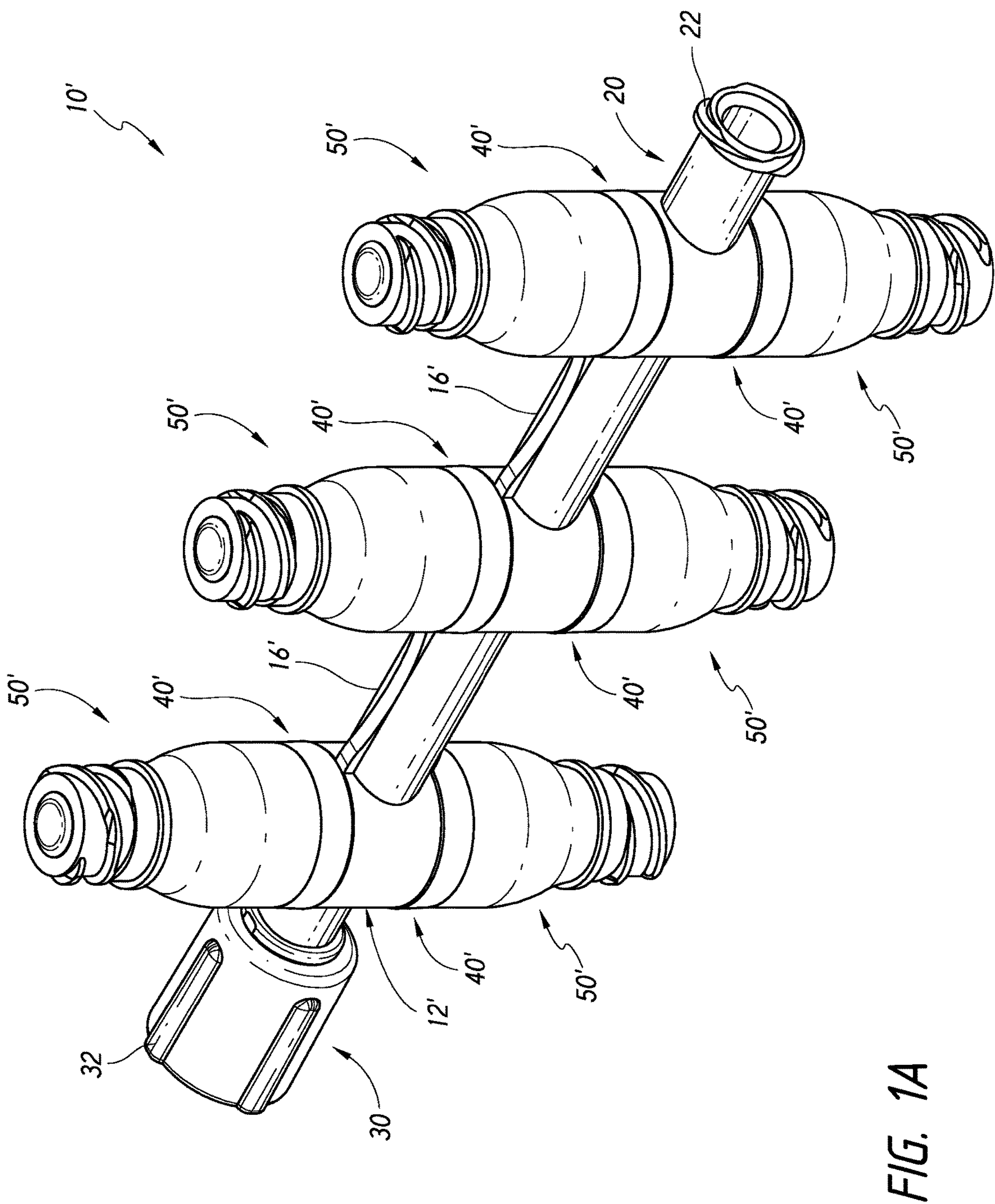
FIG. 1A is a perspective view of an embodiment of a manifold with a modified projection attachment.
Figure 1B:
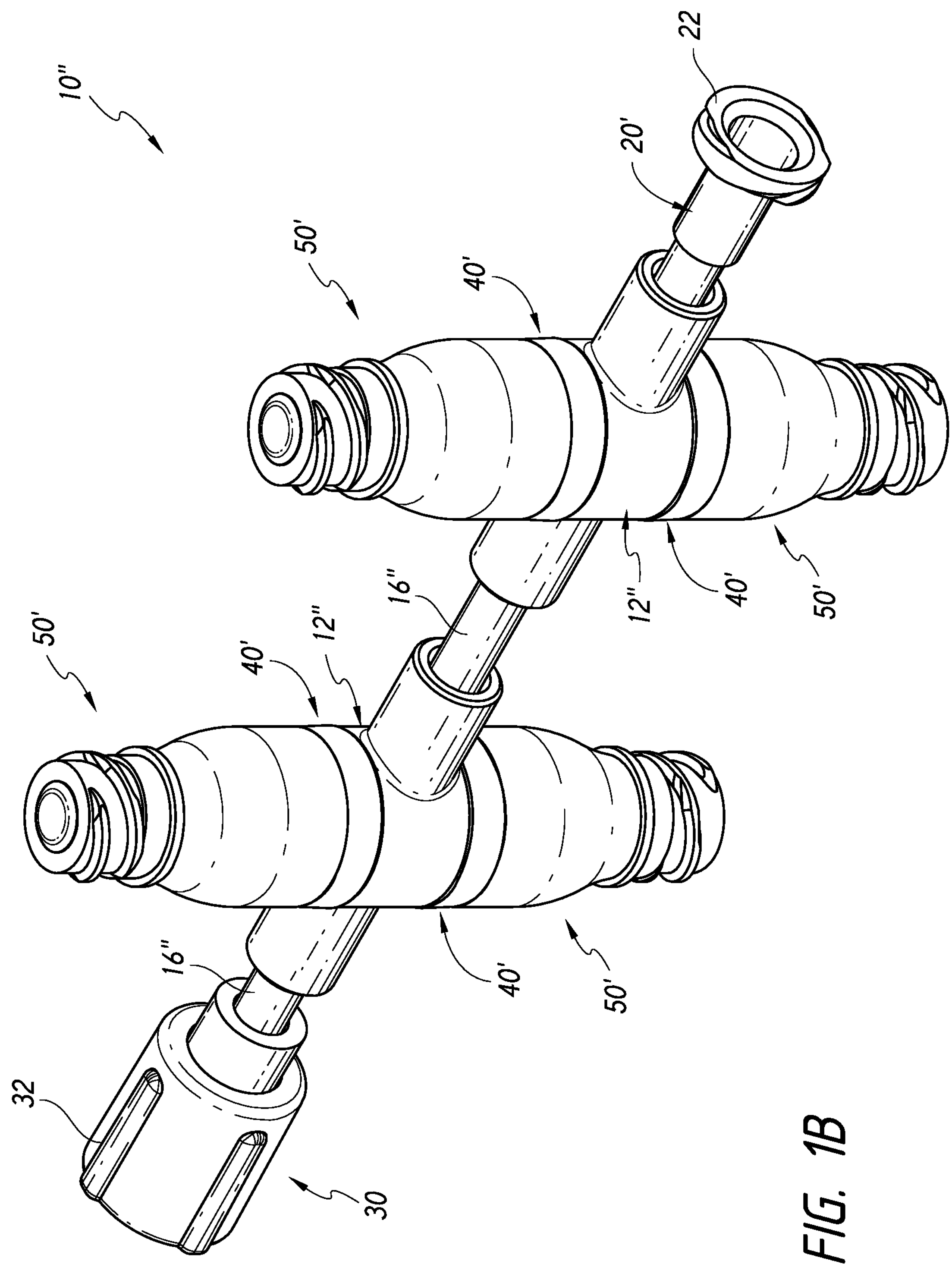
FIG. 1B is a perspective view of an embodiment of a manifold component.
Figure 2B:
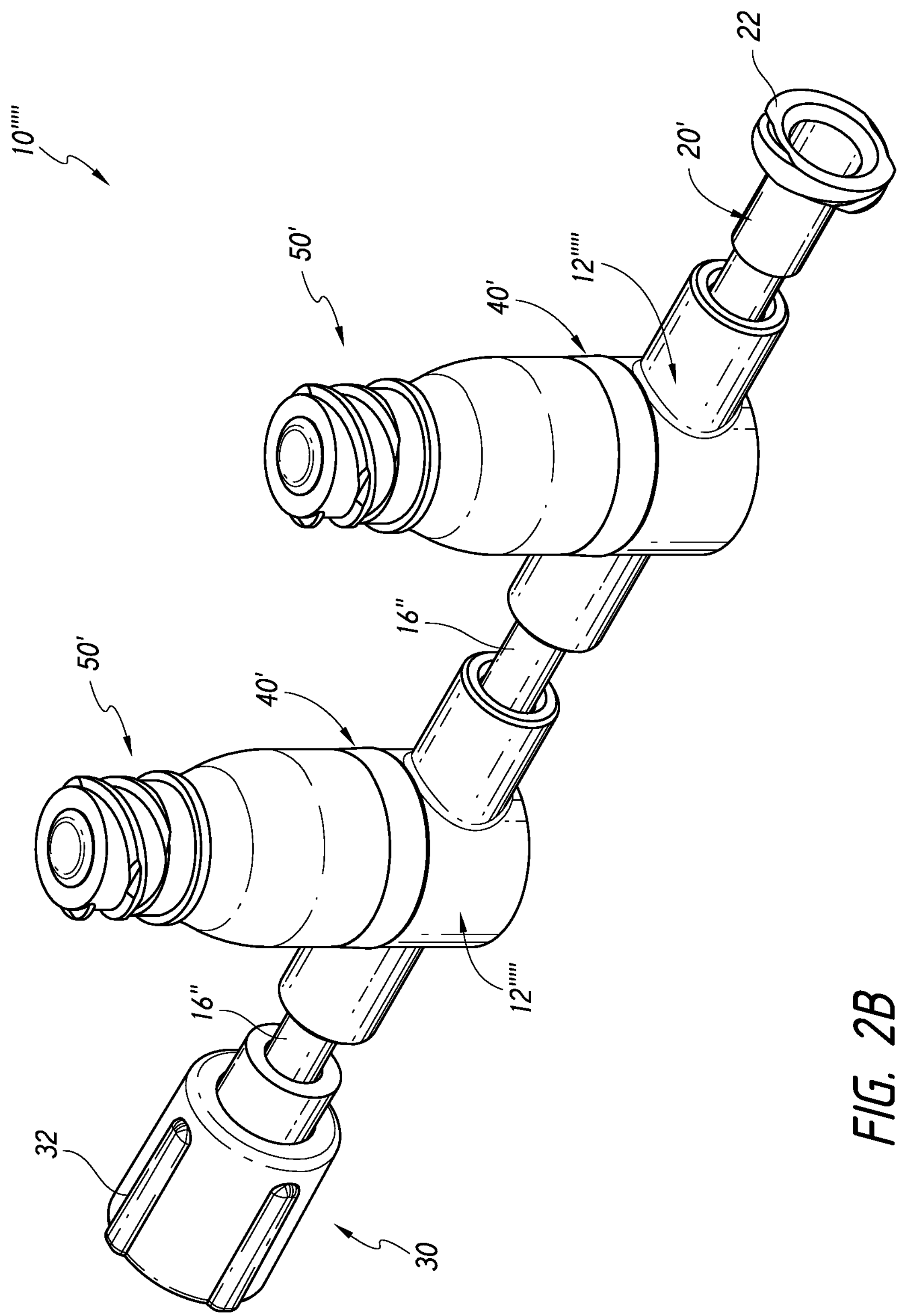
FIG. 2B is a perspective view of an embodiment of a manifold component.

Other combinations of ports are also possible. For example, FIG. 1B shows a manifold 10'' including two double housings 12''. FIG. 2B shows a manifold 10''''' including two single housings 12'''''. As discussed above, a single manifold may include various combinations of such housings as desired.

Embodiments of the invention may provide various ways to connect medical connectors to the housing ports, as discussed in greater detail below. For example, FIG. 1A shows a six port manifold 10' with alternative ports 40' and modified connectors 50'.

As shown, in some embodiments various modifications can be made to the connecting portions or joints 16 between the ports. For example, FIG. 1 shows a first version of the joints 16 while FIG. 1A shows an alternative joint 16' that includes shallow arched or curved portions. As shown in FIG. 1B, in some embodiments, rather than having a single housing 12 (see, for example, FIGS. 1 and 1A), a manifold 10'' can have a plurality of housings 12'' joined by a flexible connecting portion, for example, tubing. Thus, for example, in some embodiments the joints 16'' of the manifolds that connect housings having medical connectors or pairs of medical connectors can be formed of tubing.

FIG. 1B shows two double housings 12''. Various combinations are also possible. In some embodiments, a single housing 12'' with double ports may be provided and can be accessed by first and second ports 20' and 30. First port 20' may be similar to first port 20, except the rigid portion may be longer to accommodate the appropriate section of a medical implement, for example, a male luer. In some embodiments, the manifold may include 3 or more housings 12'' with corresponding medical connectors. Accordingly, the manifold can readily customized to provide an appropriate solution according to a user's needs. In addition, the manifold may include a combination of housings and ports, for example, a manifold may be provided with one or more double housing 12'' and one or more single housings 12''''' (see FIG. 2B). Providing flexible joints allows the manifold to flex and adapt to the needs of the user. For example, a port may be rotated to ease access while minimizing the movement of other ports that may already be accessed by various medical devices. The flexible joints of the manifold are permanently attached, for example by bonding or glueing, to their respective housings and ports such that the manifold is a single unity.

In some embodiments, various ports may remain connected or unconnected to one or more fluid sources and/or to a patient. For example, in some embodiments, one of the first port 20 and second port 30 can be connected to a patient, the other of the first port and second port may be sealed (such as with a medical connector 50 or a similar sealed access port) and unconnected to a fluid source, and one or more of the medical connectors 50 can be connected to a fluid source for the patient. In some embodiments, embodiments of the manifold can be used without a patient, for example, to combine one or more fluids into a single fluid receptacle (not shown). Accordingly, embodiments of the invention need not be used in direct connection with a patient.

Figure 3:
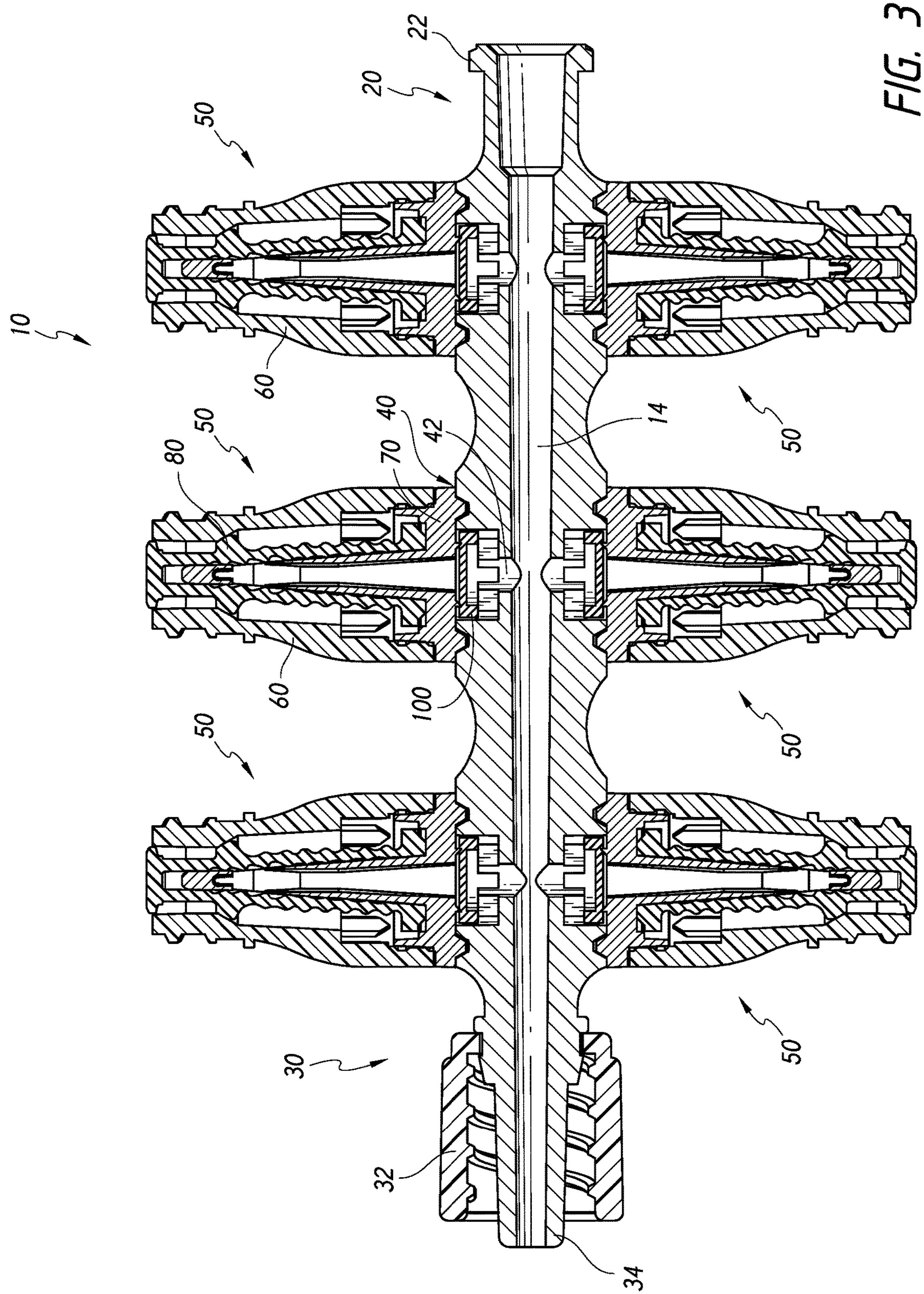
FIG. 3 is a cross-sectional view of the manifold of FIG. 1.
Figure 4:
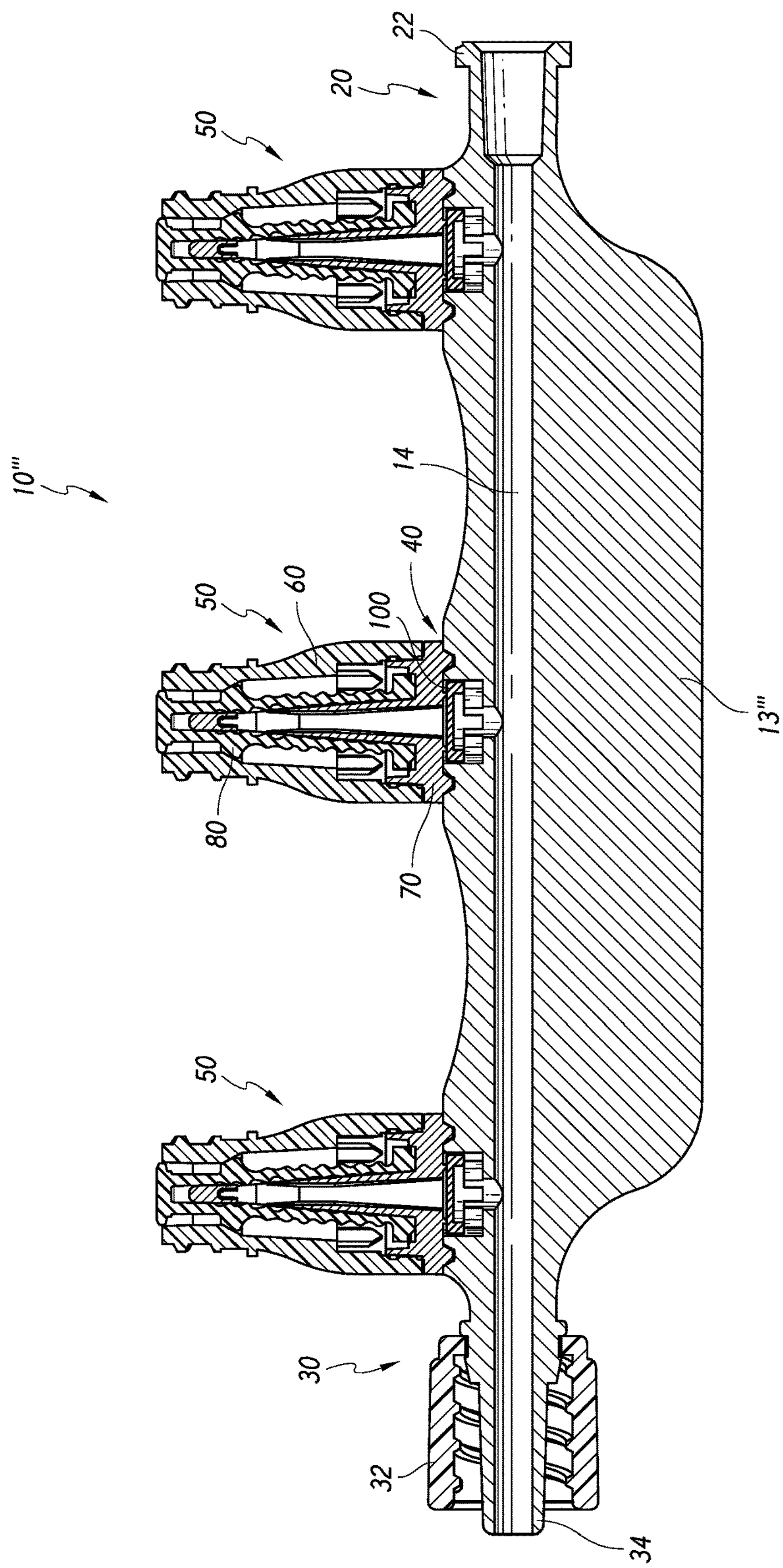
FIG. 4 is a cross-sectional view of the manifold of FIG. 2.

FIGS. 3 and 4 illustrate cross-sectional views of the manifolds of FIGS. 1 and 2, respectively. As illustrated, medical connectors 50 can attach to the manifold at access ports 40. In some embodiments, a medical connector 50 can be a needleless medical connector that includes a connector body 60, a connector base 70, and a connector valve member 80 positioned at least partially within the connector body 60. Further details regarding needless medical connectors that can be used are found in U.S. Provisional Patent Application No. 61/914,680, filed Dec. 11, 2013, the entire contents of which are hereby incorporated by reference herein and are included as an appendix to this application.

In some embodiments, other types of medical connectors or of needleless medical connectors can be attached to the access ports 40 of the manifolds. These can include connectors configured to receive syringes and connectors of varying designs. In some embodiments, a manifold can include one or more of a first type of medical connector and one or more of a second type of medical connector. In some embodiments, a manifold can include more than two types of medical connectors. In some embodiments, first port 20 and/or second port 30 may include sealed access ports that are similar to those that may be used for access ports 40. Similarly, they can include check valves such as those described herein.

Figure 3A:
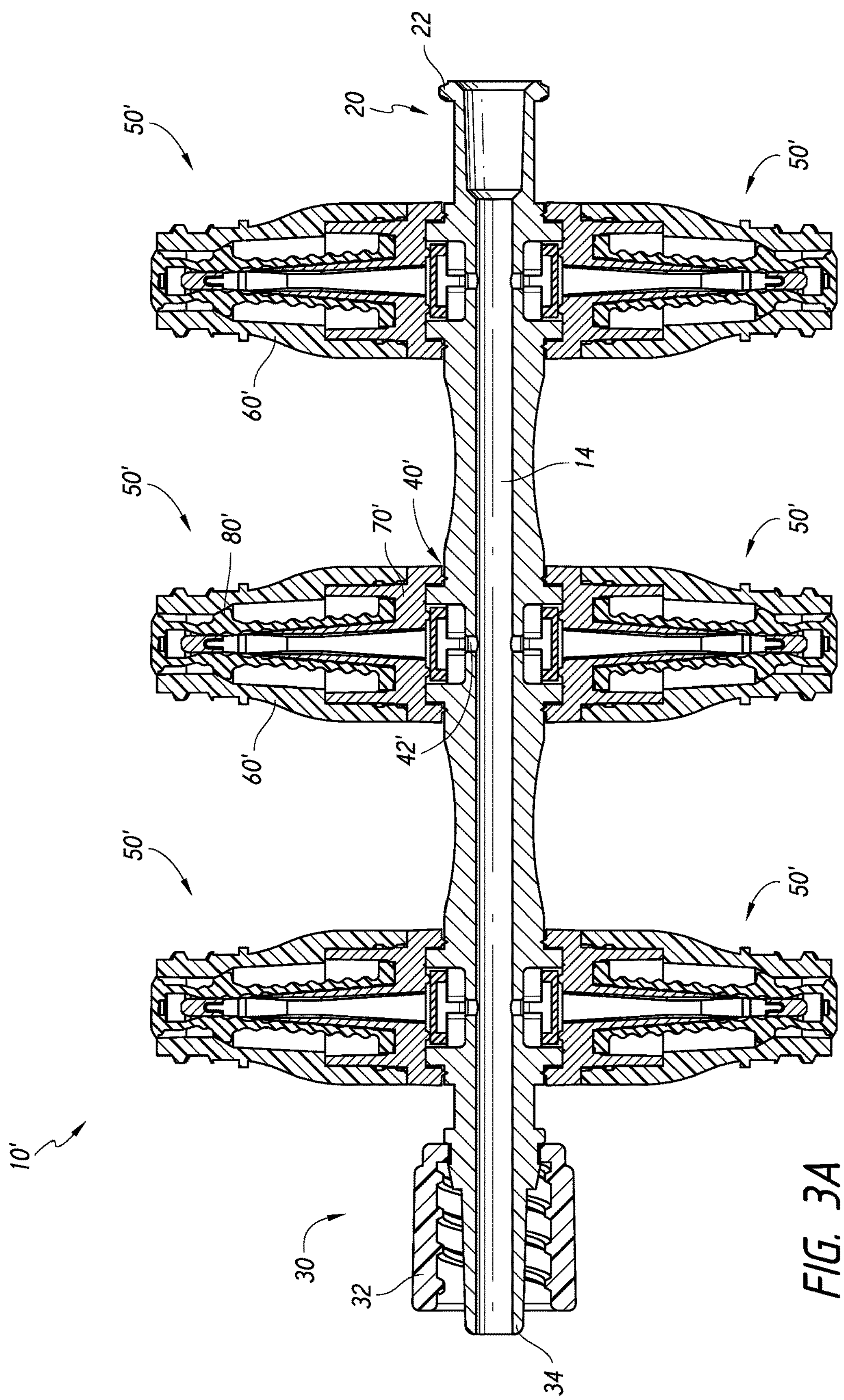
FIG. 3A is a cross-sectional view of the manifold of FIG. 1A.
Figure 4A:
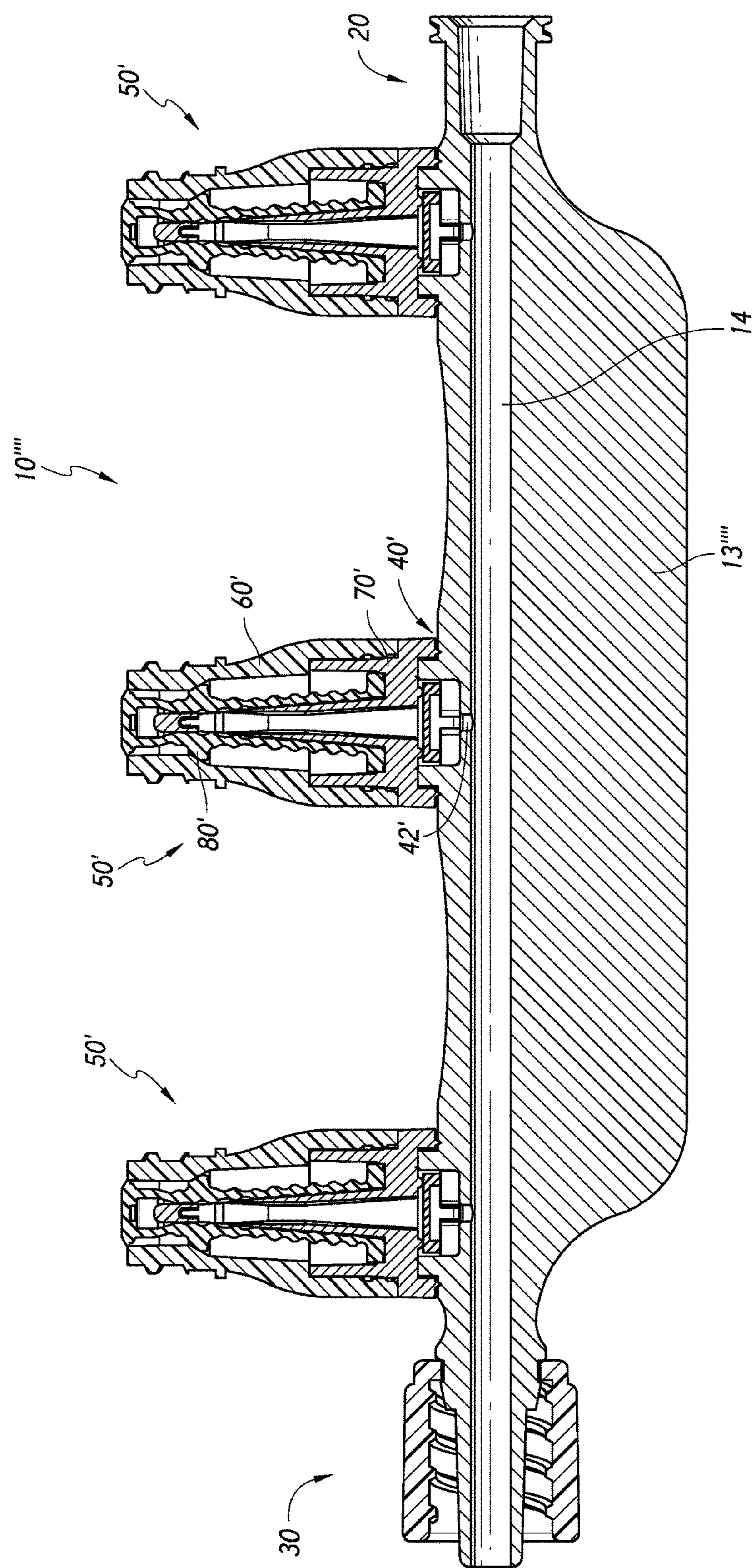
FIG. 4A is a cross-sectional view of the manifold of FIG. 2A.

FIGS. 3A and 4A illustrate cross-sectional views of the manifolds of FIGS. 1A and 2A, respectively. As illustrated, medical connectors 50' can attach to the manifold at access ports 40'. Similar to medical connector 50 discussed above, medical connector 50' can be a needleless medical connector that includes a connector body 60', a connector base 70', and a connector valve member 80' positioned at least partially within the connector body 60'. In some embodiments, the manifolds 10' and 10"" shown in FIGS. 1A, 3A and 2A, 4A, respectively, can be modified to incorporate medical connectors 50.

Figure 3B:
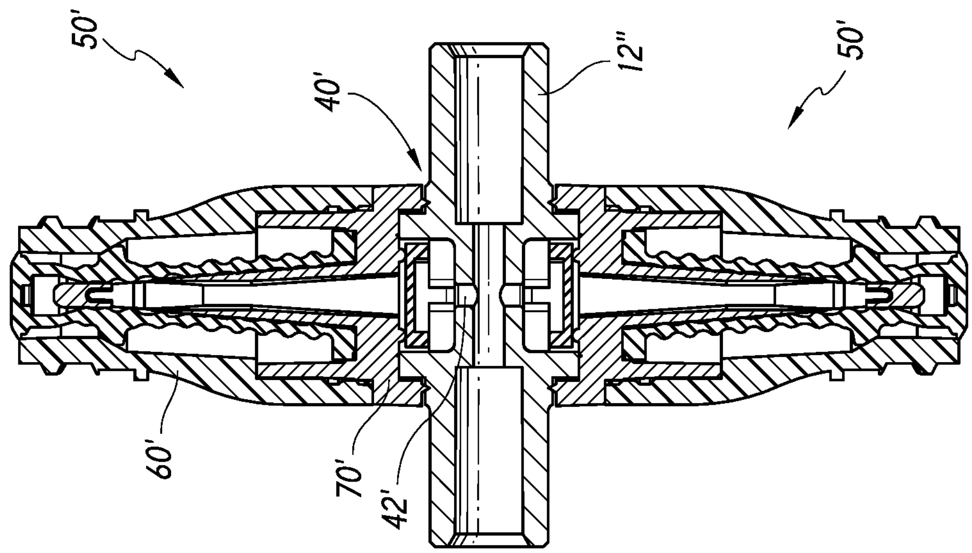
FIG. 3B is a cross-sectional view of the manifold of FIG. 1B.
Figure 4B:
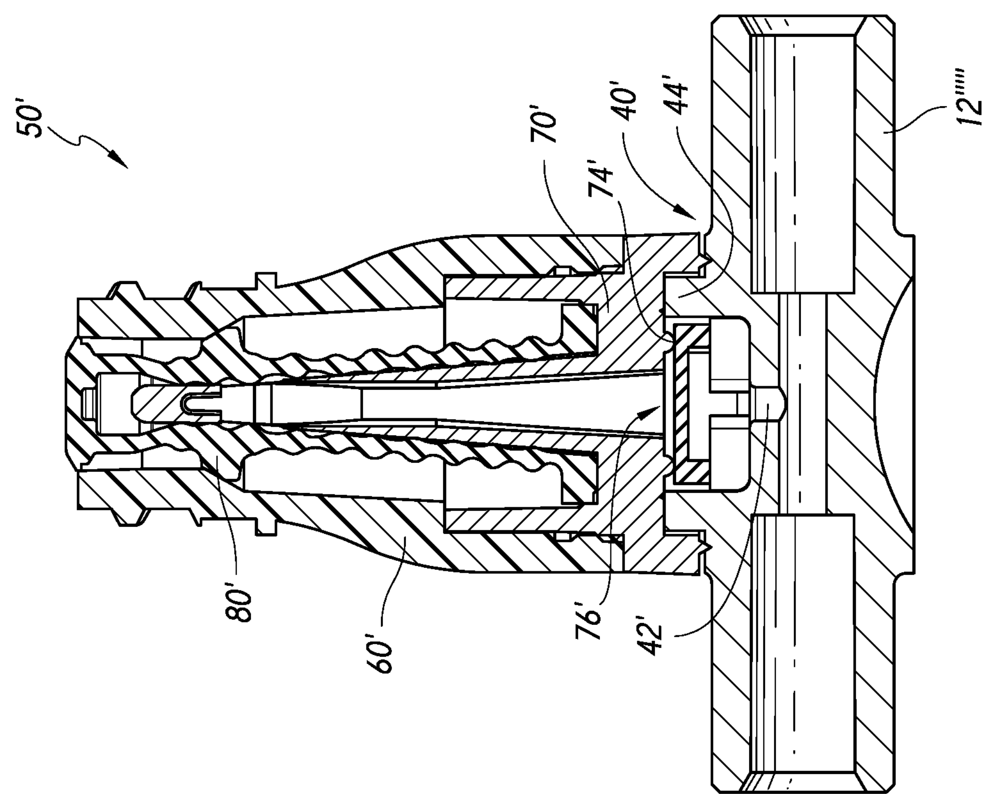
FIG. 4B is a cross-sectional view of the manifold of FIG. 2B.

FIGS. 3B and 4B illustrate cross-sectional views components of the manifolds shown FIGS. 1B and 2B, respectively. As illustrated, medical connectors 50' can attach to the manifold at access ports 40'. In some embodiments, the manifolds 10" and 10'"" shown in FIGS. 1B, 3B and 2B, 4B, respectively, can be modified to incorporate medical connectors 50.

Medical connectors can be attached to the housings in a variety of ways. As shown in FIG. 4B for example, medical connector 50' can incorporate features to facilitate sonic welding of the connector to the housing. In the illustrated embodiment, medical connector 50' is attached to housing 12'"" by way of connector base 70'. An inner recess in connector base 70' is sized to receive projecting ring 44' of access port 40'. Projecting ring can help stabilize medical connector 50' on housing 12'"".

Preferably, the medical connectors 50 can each provide a fluid flow path from a medical implement attached to the medical connector, through the medical connector, into the access port 40 and through an access channel 42 into a main channel 14 of the manifold. In a similar fashion, medical connectors 50' can each provide a fluid flow path from a medical implement attached to the medical connector, through the medical connector, and into the access port 40' and through an access channel 42' into a main channel 14 of the manifold. Preferably, the access port 40 or 40' can include a one-way valve or check valve 100, which can allow fluid to flow through the medical connector into the main channel 14, but prevent fluid from flowing from the main channel back into the medical connector. Various embodiments of a check valve 100 are described in more detail below.

Figure 5:
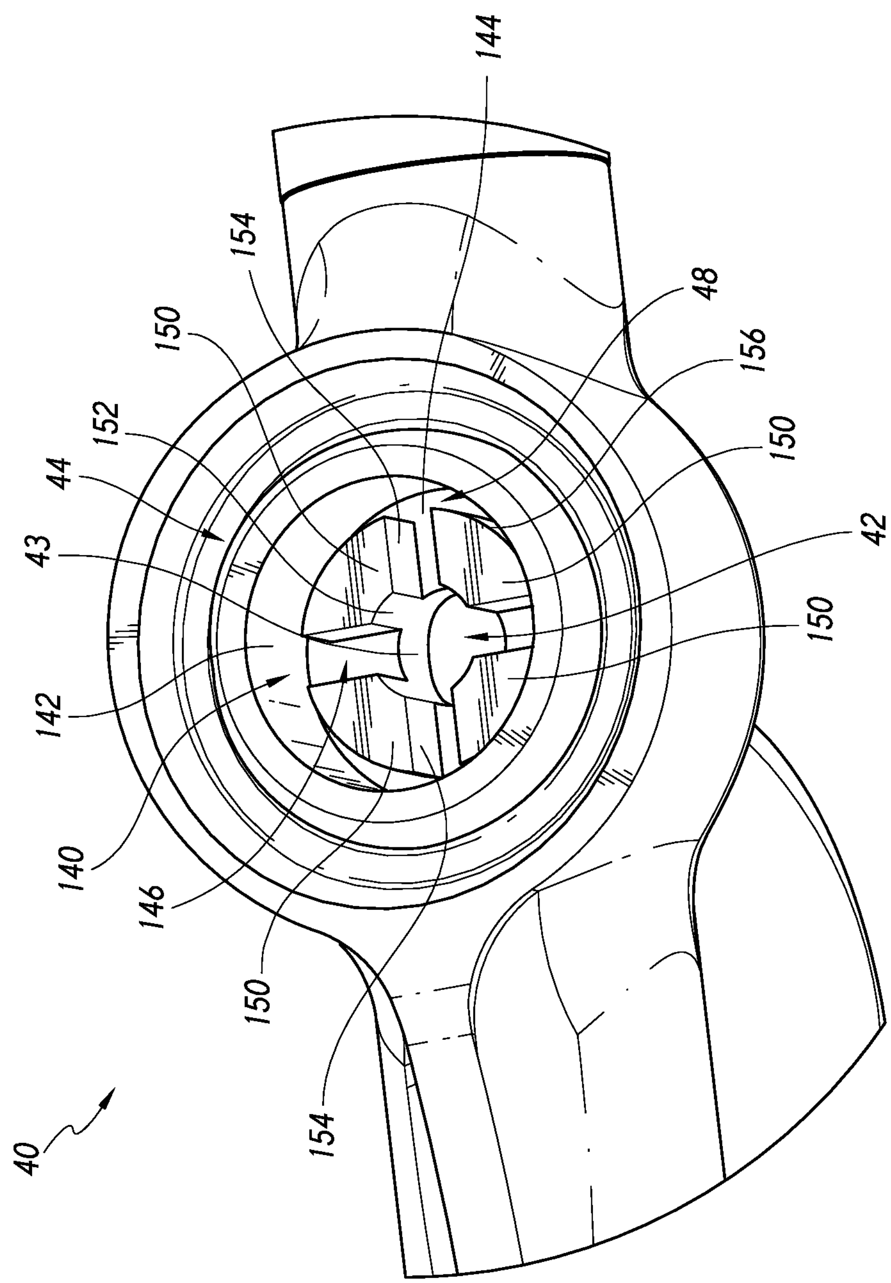
FIG. 5 is a perspective view of one embodiment of a port of a manifold.

FIG. 5 illustrates a perspective view of an access port 40 of a manifold. The access port can include a recess 140 with an outer wall 142 and a base 144. The recess is preferably cylindrical such that the outer wall is cylindrical, although in some embodiments it can have other shapes. An access channel 42 can connect the base 144 to a main channel of a manifold or other device. A plurality of protrusions 150 can extend upward from the base of the recess 140. The protrusions can each include a central wall 152 that faces the access channel 42, side walls 154, and an outer wall 156. In some embodiments, the central walls 152 of the protrusions can be flush with a side wall 43 of the access channel 42. In some embodiments, the central walls 152 can define a continuous surface with a side wall 43 of the access channel.

Preferably, the outer walls 156 of the protrusion do not extend all the way to the outer wall 142 of the access port recess 140, thereby defining an outer channel 48 between the protrusions and the outer wall 142. The protrusions can be spaced from each other to define transverse channels 46 between them that can connect the outer channel 48 to the access channel 42. In some embodiments, the access port 40 can also include an outer recess 44 that can be used to help seat a medical connector attached to the access port.

Figure 5A:
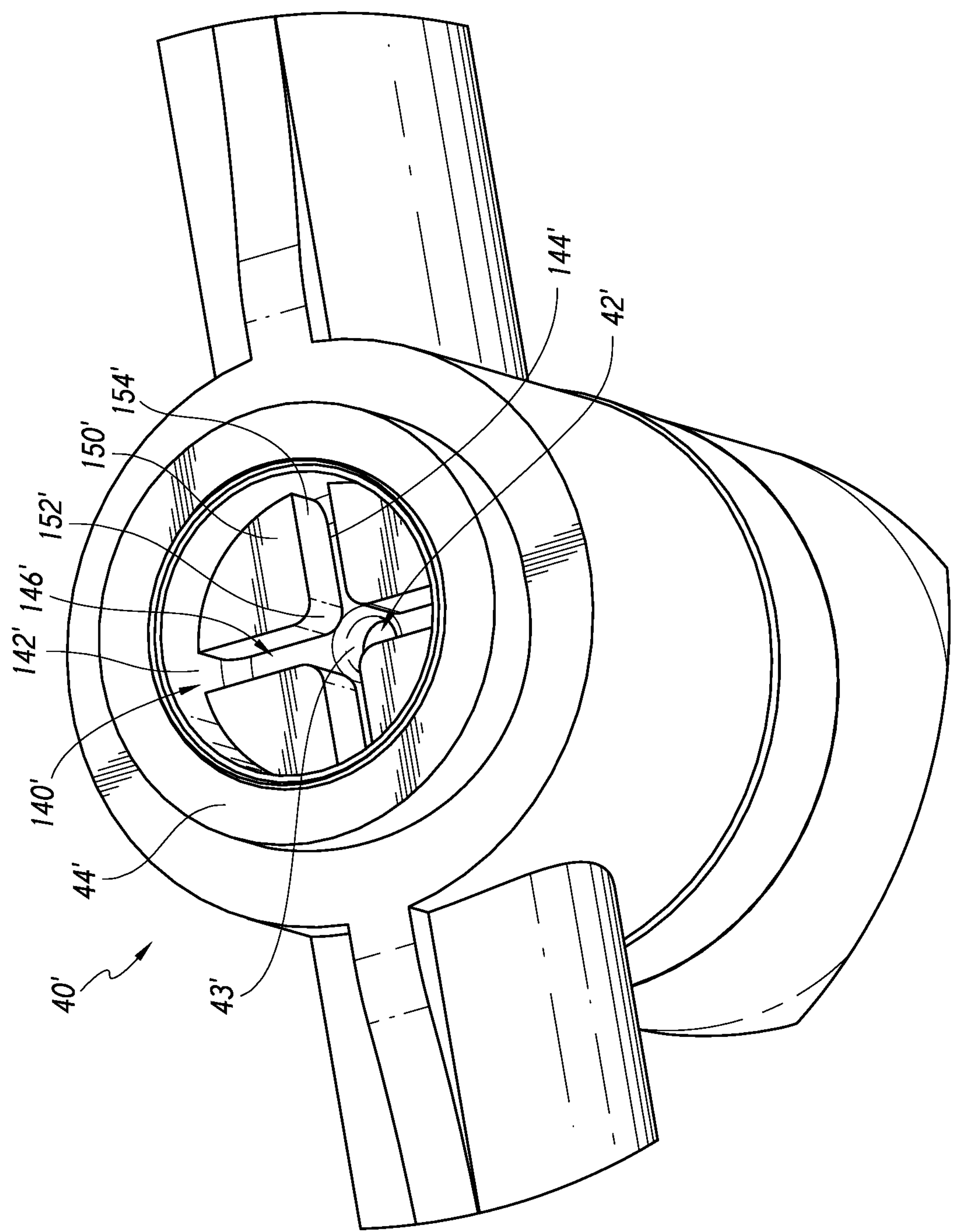
FIG. 5A is a perspective view of an embodiment of a port of a manifold.

FIG. 5A illustrates a perspective view of an access port 40' of a manifold which is similar in many respects to access port 40. The access port can include a recess 140' with an outer wall 142' and a base 144'. The recess is preferably cylindrical such that the outer wall is cylindrical, although in some embodiments it can have other shapes. An access channel 42' can connect the base 144' to a main channel of a manifold or other device. A plurality of protrusions 150' can extend upward from the base of the recess 140'. The protrusions can each include a central wall 152' that faces the access channel 42' and side walls 154'. In some embodiments, the central walls 152' of the protrusions can be recessed back from a side wall 43' of the access channel 42' as shown. The transition from the central walls 152' to the side wall 43' may be curved to facilitate fluid flow there through. In some embodiments, the central walls 152' can define a continuous surface with a side wall 43' of the access channel. As shown, the protrusions 150' may be formed flush with the outer wall 142' though in some embodiments, they may be off set from the wall and provide an outer fluid channel like channel 48 shown in FIG. 5. Access port 40' may also include projecting ring 44' that may be used to stabilize connector 50' as shown.

Figure 6:
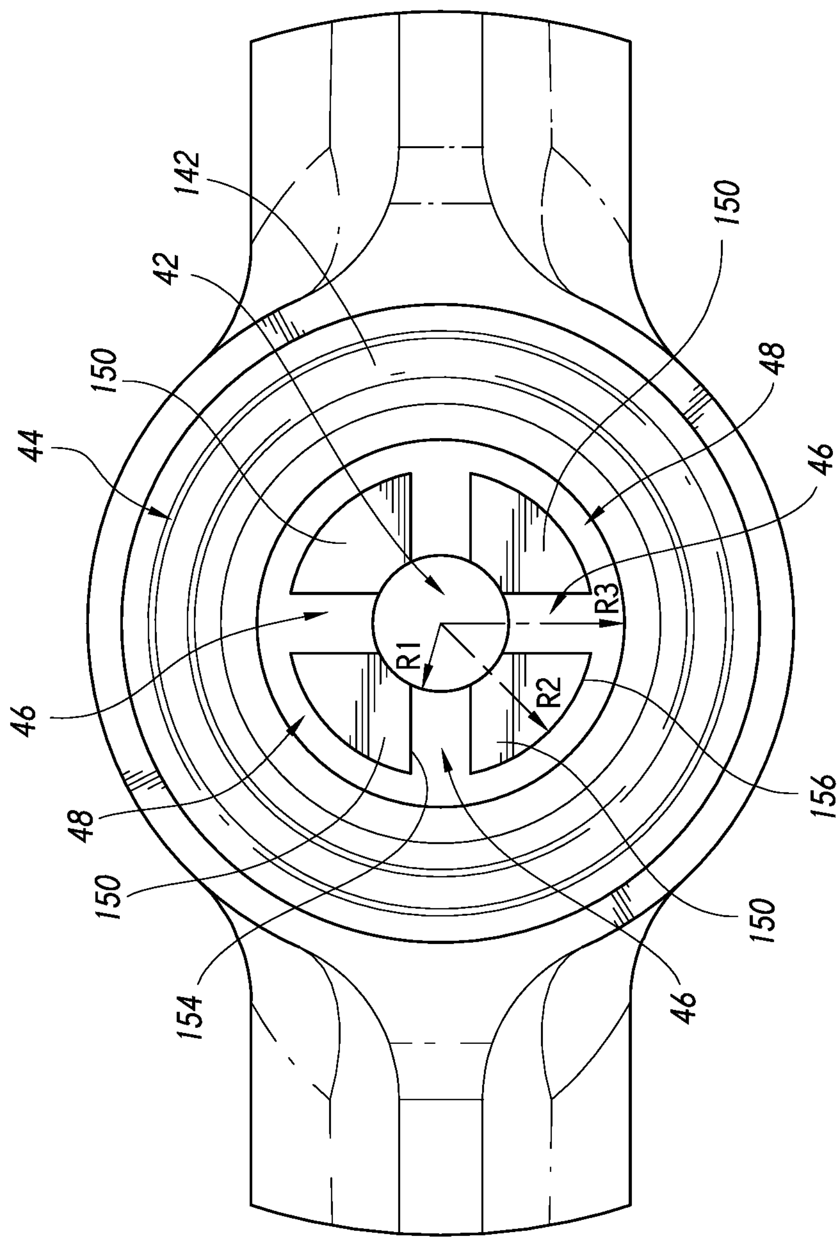
FIG. 6 is a top view of the port of FIG. 5.

FIG. 6 illustrates a top view of an access port 40. In the embodiment of FIG. 6, the access port includes four protrusions 150 that are spaced symmetrically about a center of the access channel 42. Preferably, side walls 154 of the protrusions are generally parallel to each other. In some embodiments, however, the side walls can angle toward each other as they get closer to the center of the access channel 42, and in some embodiments the side walls can diverge as they get closer toward the center of the access channel. In some embodiments, the access port 40 can include varying numbers of protrusions 50, such as 2, 3, 5, 6, or more protrusions. The protrusions can be symmetrically spaced about the access channel 42 or spaced about the access channel in other arrangements.

In some embodiments, various components of the access port 40 can be centered around the access channel 42. In some embodiments, the access channel itself can be generally cylindrical and have a radius $R_1$, as illustrated. In some embodiments the outer wall 142 of the access port recess 140 can have a radius $R_3$ centered on the center of the access channel 42. Similarly, the outer walls 156 of the protrusions 150 can be curved and have a radius of curvature R2 centered on the center of the access channel 42. Similar radius of curvatures may be defined by access port 40'. In the illustrated embodiment, R2' and R3' of access port 40' would be equal.

When fluid flows through a medical connector attached to an access port 40, it will flow through the channels of the access port in order to reach a main channel of a fluid flow line. In various embodiments, the sizing of certain components of the access port can affect the size of the outer channel 48, transverse channels 46, and/or access channel 42, and therefore can affect the fluid flow characteristics of the access port 40.

Thus, for example, in some embodiments the ratio of the radius $R_3$ of the access port recess 140 to the radius $R_2$ of the outer walls 156 of protrusions 150 may vary. In some embodiments, the ratio of $R_3$ to $R_2$ can be between approximately 0.5 and 2.0. In some embodiments, the ratio of $R_3$ to $R_2$ can be between approximately 0.8 and 1.7. In some embodiments, the ratio of $R_3$ to $R_2$ can be between approximately 1.0 and 1.5. In some embodiments, the ratio of $R_3$ to $R_2$ can be between approximately 1.1 and 1.3. These ratios are also applicable to access port 40'.

Similarly, in some embodiments the ratio of the radius $R_3$ of the access port recess 140 to the radius $R_1$ of the access channel 42 may vary. In some embodiments, the ratio of $R_3$ to $R_1$ can be between approximately 2.0 and 3.3. In some embodiments, the ratio of $R_3$ to $R_1$ can be between approximately 2.3 and 3.0. In some embodiments, the ratio of $R_3$ to $R_1$ can be between approximately 2.5 and 2.8. In some embodiments, the ratio of $R_3$ to $R_1$ can be between approximately 2.6 and 2.7. These ratios are also applicable to access port 40'.

Further, in some embodiments the ratio of the radius $R_2$ of the outer walls 156 of protrusions 150 to the radius $R_1$ of the access channel 42 may vary. In some embodiments, the ratio of $R_2$ to $R_1$ can be between approximately 1.5 and 2.9. In some embodiments, the ratio of $R_2$ to $R_1$ can be between approximately 1.8 and 2.6. In some embodiments, the ratio of $R_2$ to $R_1$ can be between approximately 2.1 and 2.3. These ratios are also applicable to access port 40'.

Figure 7:
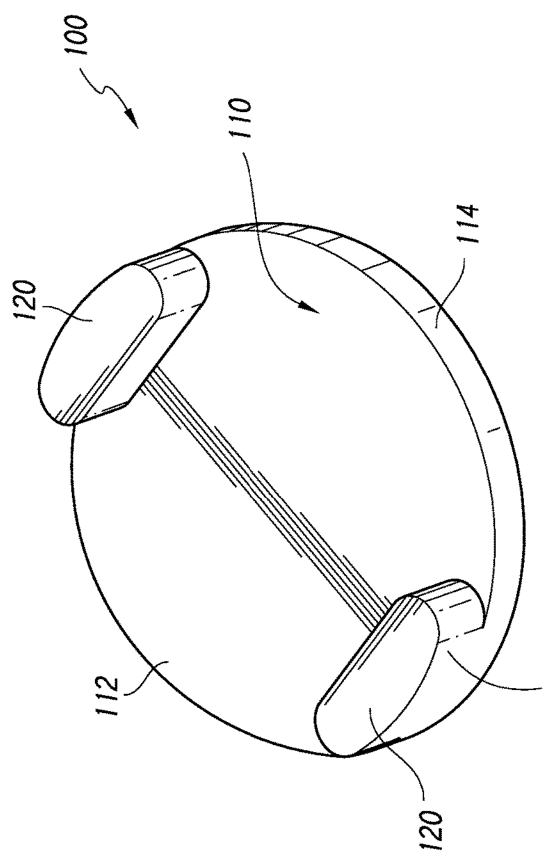
FIG. 7 is a bottom perspective view of one embodiment of a check valve.
Figure 8:
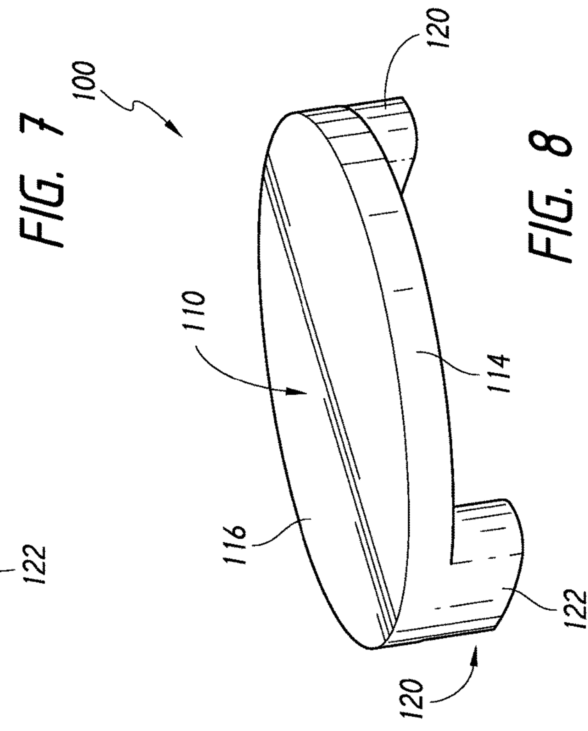
FIG. 8 is a top perspective view of the check valve of FIG. 7.

FIGS. 7 and 8 illustrate perspective views of a check valve 100 that can be positioned within an access port 40 or 40'. FIG.7 illustrates a bottom perspective view and FIG. 8 illustrates a top perspective view. The check valve preferably includes a diaphragm 110 having a bottom or lower surface 112, a side wall 114, and a top or upper surface 116. The diaphragm is preferably solid, although in some embodiments it can have perforations. A plurality of supports 120 can extend from the bottom or lower surface 112 of the diaphragm. The supports can be used to provide space for the diaphragm to flex from a closed to an open position, discussed in more detail below. Preferably, the diaphragm and supports are integrally formed (e.g., they may be molded as a single piece), although in some embodiments they may be formed of separate components.

The supports can have an outer wall 122 that is preferably flush with and forms a continuous surface with the side wall 114 of the diaphragm. In some embodiments, however, the supports 120 can be inset from the side wall 114 such that there is a portion of the bottom surface 112 between the supports 120 and the side wall 114.

Figure 9:
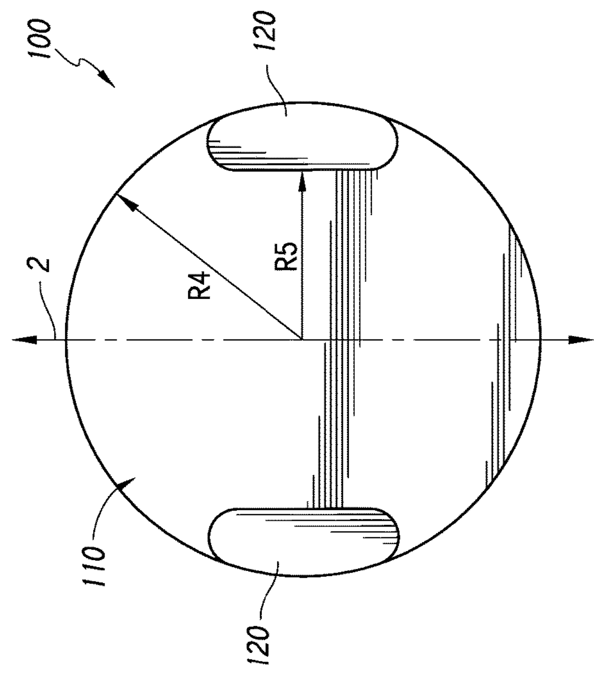
FIG. 9 is a bottom view of the check valve of FIG. 8.

FIG. 9 illustrates a bottom view of the valve 100. The valve is preferably circular with a radius $R_4$, although in some embodiments the valve can have other shapes, such as a square, oval, rectangle, etc. In some embodiments, the radius $R_4$ can be approximately equal to the radius $R_3$ of the access port recess 140, such that the valve 100 can fit flush within the recess. In some embodiments, the radius $R_4$ can be slightly or substantially smaller than the radius $R_3$ such that a gap exists between the side walls 114 of the valve 100 and the side walls 142 of the access port recess when the valve is centered in the access port recess. The existence of a gap can make manufacturing of the valve easier. Varying the size of the gap can also affect flow rates through the valve. In some embodiments, the radius $R_4$ can be between approximately 0.02 inches and approximately 0.09 inches smaller than the radius $R_3$. In some embodiments, the radius $R_4$ can be between approximately 0.03 inches and approximately 0.08 inches smaller than the radius $R_3$. In some embodiments, the radius $R_4$ can be between approximately 0.05 inches and approximately 0.06 inches smaller than the radius $R_3$.

In some embodiments, as illustrated, the supports 120 can be positioned approximately 180 degrees apart about the center of the valve. The valve can have an axis of symmetry 2 that bisects the valve and does not pass through either support, as illustrated. In some embodiments, the valve can have more than two supports 120, with pairs positioned approximately 180 degrees apart from each other. For example, a valve could have four supports, each 90 degrees apart, and multiple axes of symmetry that bisect the valve and do not pass through any of the supports. In some embodiments, the axis of symmetry can define how the valve deforms if it experiences a pressure differential between its bottom surface 112 and its top surface 116. For example, in the illustrated embodiment, a positive net pressure on the top surface of the valve member would cause the valve member to bend, buckle, or curve generally about the axis of symmetry or an axis that is parallel to the axis of symmetry.

In some embodiments, the supports 120 can all be positioned the same minimum distance $R_5$ from the center of the valve. In some embodiments, one or more of the supports can have a different minimum distance from the center of the valve than one or more of the other supports, in which case $R_5$ can refer to the minimum distance from the center of the valve to the closest support 120. In some embodiments, the relationship between the distance $R_5$ and $R_4$ can affect how easily the valve member deforms as a result of differential pressures on the top surface 116 and bottom surface 112 of the diaphragm 110. In some embodiments, for example, the ratio of $R_4$ to $R_5$ can be between approximately 1.2 and approximately 1.8. In some embodiments, the ratio of $R_4$ to $R_5$ can be between approximately 1.3 and approximately 1.6. In some embodiments, the ratio of $R_4$ to $R_5$ can be between approximately 1.3 and approximately 1.5. In some embodiments, the ratio of $R_4$ to $R_5$ can be between approximately 1.35 and approximately 1.45. In some embodiments, the ratio of $R_4$ to $R_5$ can be greater than 1.8 or less than 1.2.

Figure 10:
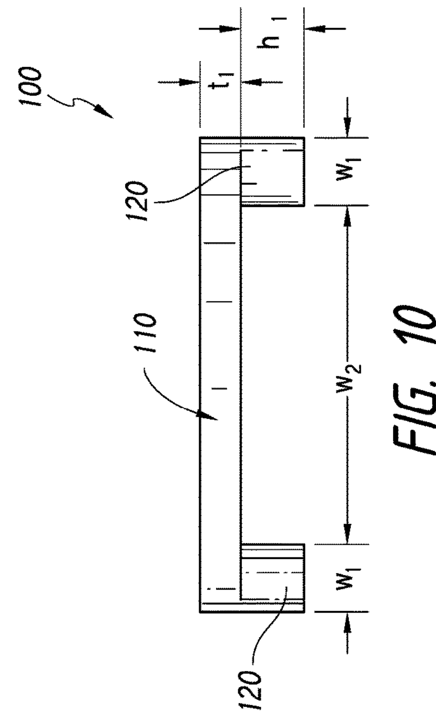
FIG. 10 is a side view of the check valve of FIG. 9.

FIG. 10 illustrates a side view of the valve 100, oriented such that the axis of symmetry 2 is perpendicular to the illustrated plane. In various embodiments, the sizing of the diaphragm 110 and supports 120 can be modified to adjust the pressure differential required for the valve member to bend or buckle. For example, the supports can have a width $w_1$ and the distance between the supports can have a width $w_2$. Similarly, the diaphragm can have a thickness $t_1$ and the supports can have a height $h_1$. In some embodiments, the ratio of the width $w_2$ to the thickness $t_1$ can affect the ability of the valve to resist pressure differentials. In some embodiments, the ratio of the width $w_2$ to the thickness $t_1$ can be between approximately 7 and approximately 10. In some embodiments, the ratio of the width $w_2$ to the thickness $t_1$ can be between approximately 7.5 and approximately 9.5. In some embodiments, the ratio of the width $w_2$ to the thickness $t_1$ can be between approximately 8 and approximately 9. In some embodiments, the ratio of the width $w_2$ to the thickness $t_1$ can be between approximately 8.2 and approximately 8.5.

In some embodiments, the ratio of the width $w_2$ to the height $h_1$ of the supports can affect how easily and how much the diaphragm 110 can bend when the valve is in an open position, discussed below. This can also affect the ability of the valve to handle high flow rates and/or how quickly the valve opens to allow fluid flow. In some embodiments, the ratio of the width $w_2$ to the height $h_1$ can be between approximately 3 and approximately 8. In some embodiments, the ratio of the width $w_2$ to the height $h_1$ can be between approximately 4 and approximately 7. In some embodiments, the ratio of the width $w_2$ to the height $h_1$ can be between approximately 4.5 and approximately 6.5. In some embodiments, the ratio of the width $w_2$ to the height $h_1$ can be between approximately 5 and approximately 6.

Figure 11B:
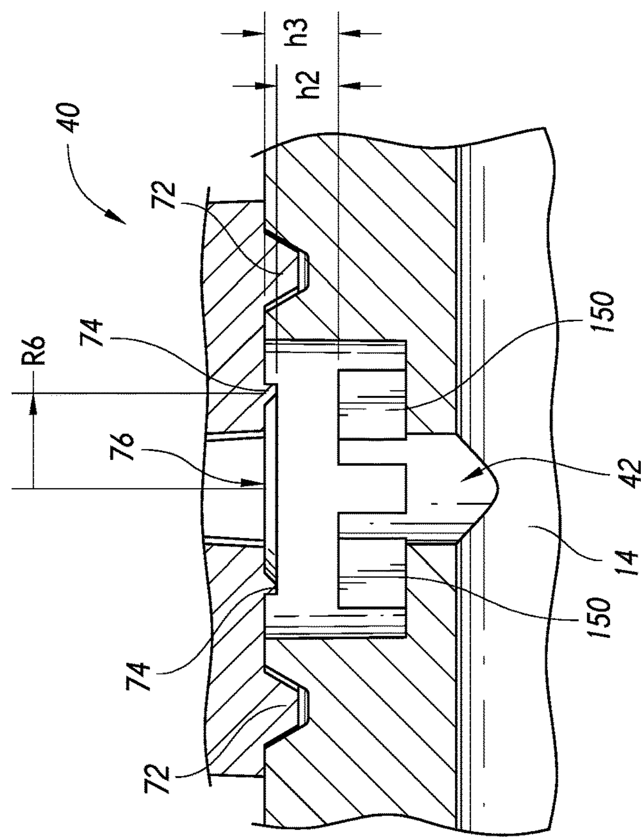
FIG. 11B is a cross-sectional view of one embodiment of a port of a manifold with an attached medical connector, with a check valve not shown.
Figure 11A:
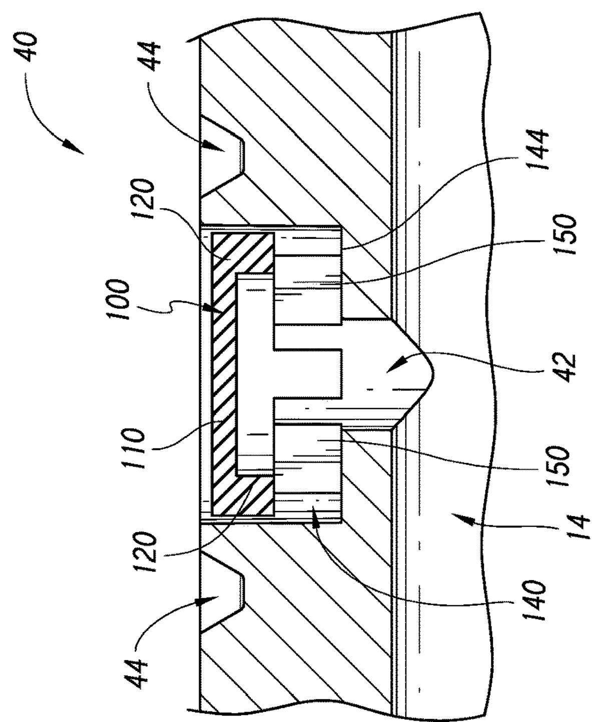
FIG. 11A is a cross-sectional view of one embodiment of a port of a manifold with a check valve.

FIG.11A illustrates a valve 100 positioned within an access port 40, as described above. The supports 120 can be positioned on the protrusions 150 to lift the diaphragm above the protrusions. In some embodiments, the access port recess 140 can have no protrusions and the supports of the valve can be positioned directly on the base 144 of the recess or on the base of any recessed portion of a flow channel. Thus, for example, in some embodiments the valve can be positioned within an inlet and/or an outlet port of a manifold, extension set, or other connection systems. In some embodiments, the valve can be positioned within a medical connector that has only a single inlet and outlet port.

FIG. 11B illustrates a cross-sectional view of an access port 40 that has a medical connector attached to the access port. The access port can have a valve 100, which is not shown for illustrative purposes. As shown in FIG. 11B, when a medical connector is attached to an access port there can be a height $h_2$ between a ring 74 of the medical connector and a top surface of the protrusions 150 extending from the base of the recess 140. There can also be a height $h_3$ between a bottom surface of the base 70 of the medical connector (excluding any ring 74) and the top surface of the protrusions 150. Also visible in FIG. 11B is an inner radius $R_6$ of the ring 74 of the medical connector (i.e., a radius from the center of the ring to an inner surface of a wall that forms the ring).

Figure 12B:
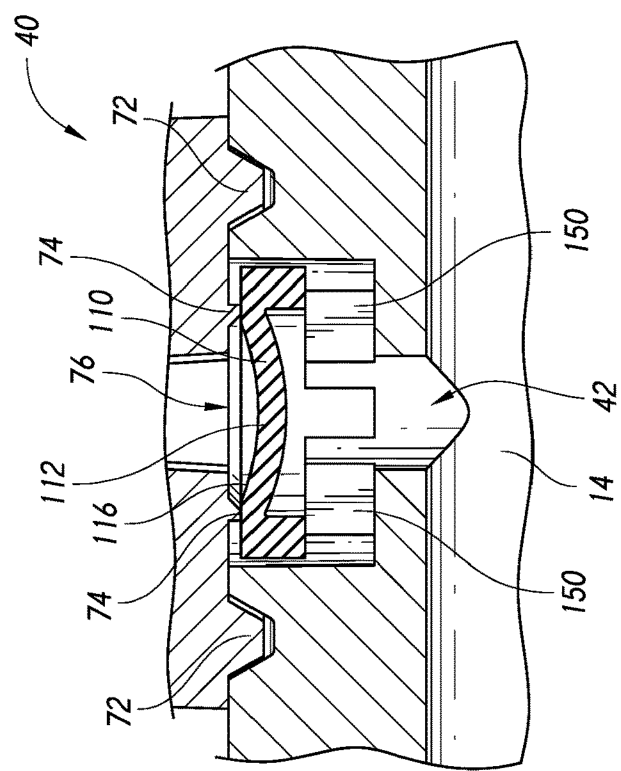
FIG. 12B is a cross-sectional view of the embodiment of FIG. 12A with the check valve in an open position.
Figure 12A:
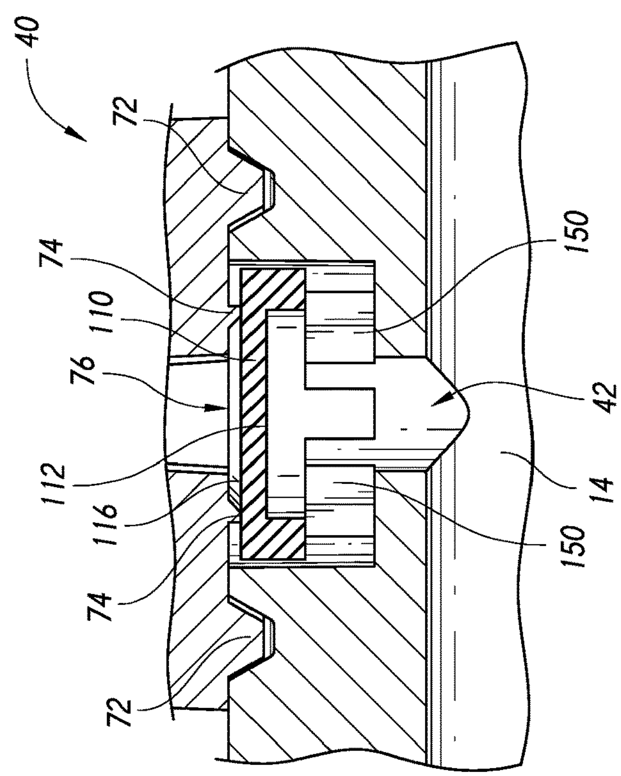
FIG. 12A is a cross-sectional view of one embodiment of a port of a manifold with an attached medical connector and a check valve in a closed position.

FIGS. 12A and 12B illustrate a cross-sectional view of an access port 40 that includes a valve member 100 and that has a medical connector 50 attached to the access port. In some embodiments, a base 70 of the medical connector can have an annular projection 72 that can be used to help attach the medical connector to the access port such as by sonic welding or gluing. Other forms of attachment are also possible, including snap fit constructions. In the illustrated embodiment, projection 72 is preferably glued into outer recess 44.

FIG. 12A illustrates the valve member 100 in a closed position and FIG. 12B illustrates the valve member in an open position. The valve is oriented the same as in FIG. 10, such that the axis of symmetry of the valve is perpendicular to the plane of the figure. In the closed position, the diaphragm 112 of the valve can be generally flat on both sides and can seal against the base 70 of the medical connector. In some embodiments, as illustrated, the medical connector can have a ring 74 or other projection that can be sized and configured to contact and seal against the diaphragm 110 of the valve 100 when the valve is in a closed position. As shown in FIG. 4B, medical connector 50' may include a similar ring 74'.

In some embodiments, the medical connector 50 and/or the access port 40 can be sized and configured such that the base 70 of the medical connector or the ring 74 can compress at least a portion of the valve 100. This can help create the seal between the diaphragm 110 and the medical connector. Thus, in embodiments where the diaphragm seals against a ring 74 or other projection of the medical connector, the height $h_2$ (shown in FIG. 11B) can be less than the total height of the valve member 100 (i.e., the sum of $h_1$ and $t_1$, illustrated in FIG. 10). Similarly, in embodiments where the connector does not have a ring or other projection, the height $h_3$ (shown in FIG. 11B) can be less than the total height of the valve member. In various embodiments, the relative differences between the heights can affect the amount of sealing. For example, in some embodiments the ratio of the total height of the valve member to the height $h_2$ can be between approximately 1.0 and approximately 1.5. In some embodiments, the ratio of the total height of the valve member to the height $h_2$ can be between approximately 1.0 and approximately 1.3. In some embodiments, the ratio of the total height of the valve member to the height $h_2$ can be between approximately 1.0 and approximately 1.2. In some embodiments, the ratio of the total height of the valve member to the height $h_2$ can be between approximately 1.1 and approximately 1.2. In embodiments without a sealing ring 74 or other projection, various ratios of the total height of the valve member to the height $h_3$ can be as described with respect to the height $h_2$. In some embodiments, the total height of the valve member can be less than the height $h_2$ such that the valve member functions as a floating check valve. In some such instances, the supports 120 on the bottom surface of the diaphragm 110 may provide stability and prevent inversion of the diaphragm. Similar ratios are applicable to medical connector 50'.

In various embodiments, the relationship between the radius $R_6$ of a ring 74 (shown in FIG. 11B) and the distance $R_5$ between supports 120 and the center of the valve (shown in FIG. 10) can affect how the valve deforms in response to a compressive force from the ring and any resulting change in a seal between the ring and the valve and/or in a cracking pressure of the valve (described further below). Preferably, $R_5$ can be approximately equal to $R_6$. In some embodiments, $R_5$ can be smaller than $R_6$. In some embodiments, $R_5$ can be greater than $R_6$. In some embodiments, the relationship between $R_5$ and $R_6$ can be varied according to the durometer of the check valve 100 in order to ensure that the valve seals as desired. Similar adjustments can be made to medical connector 50'.

If a negative pressure differential exists on the diaphragm between the bottom surface 112 and the upper or top surface 116—i.e., a net negative pressure on the top surface—the pressure will tend to push the diaphragm against the base 70 or inner annular projection 74, which can create or enhance a seal and prevent fluid from flowing into the medical connector. In contrast, if there is a positive pressure differential—i.e., a positive net pressure on the top surface 116—the diaphragm 110 will tend to deform as described above and move the valve from a closed to an open position, as illustrated in FIG. 12B. In the open position, the valve can flex downward (creating a concavity on its top surface), allowing fluid to flow through an opening 76 in the base of the medical connector, into the access port recess 140, and through the access channel 42 to reach the main channel 14.

In some embodiments, at least a portion of the valve member 100 remains stationary as the valve transitions between an open and closed position. This can help the valve move more easily from an open to a closed position to help prevent undesired retrograde flows. It can also allow for designs that transition from a closed to an open position at lower pressures, as described further below. In some embodiments, at least a portion of the diaphragm can remain in generally the same location when the valve is in an open position as when the valve is in a closed position. In some embodiments, at least a portion of the diaphragm 110 can remain in contact with the base 70 of a medical connector when the valve is in the open position.

In some embodiments, the valve 100 can be formed of a resilient material such that, absent a pressure differential, the valve tends to move toward the closed position (i.e., is biased toward the closed position).

As described above, the valve can be designed differently to affect how easily it moves from a closed to an open position. The pressure differential required to move the valve 100 from a closed to an open position can be referred to as the cracking pressure. In some embodiments, the valve can have a minimal cracking pressure, such that the valve very easily transitions from a closed to an open position. This can make it easier to pass fluids through the valve and into a main fluid flow line. It also allows the valves to work effectively with high flow rate connectors (such as, for example, connectors that allow flow rates of 450 mL/min or even greater). In some embodiments, the valve can have a cracking pressure that is at or below approximately 5 psi. In some embodiments, the valve can have a cracking pressure that is at or below approximately 4 psi. In some embodiments, the valve can have a cracking pressure that is at or below approximately 3 psi. In some embodiments, the valve can have a cracking pressure that is at or below approximately 2 psi. In some embodiments, the valve can have a cracking pressure that is at or below approximately 1 psi. In some embodiments, the valve can have a cracking pressure that is less than the pressure exerted on the valve from fluid in a reservoir hanging on a standard IV pole. In some embodiments, this can be approximately equal to the pressure of 36 inches of water. In some embodiments, this can be approximately equal to 1.3 psi.

In some embodiments, the cracking pressure can be zero, such that even with zero pressure differential between the lower 112 and upper 116 surfaces of the diaphragm 110 the valve will be in an open position. In other words, in some embodiments the closed position of the valve is not an equilibrium position of the valve. In such embodiments, the valve may not be in a closed position until a retrograde fluid flow creates a negative pressure differential on the diaphragm 110. In some embodiments with a zero cracking pressure, the valve can function as a floating check valve, as described, for example, above.

Figure 13A:
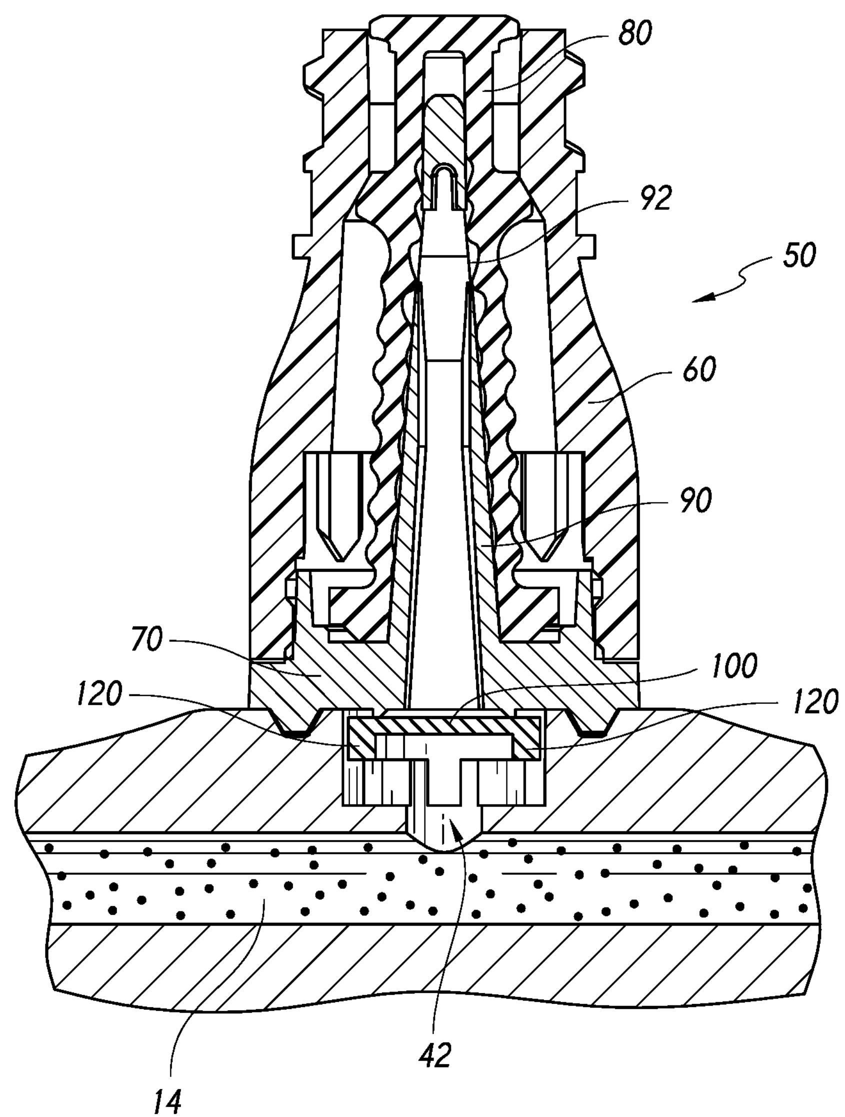
FIG. 13A is a cross-sectional view of one embodiment of a port of a manifold with an attached medical connector and a check valve in a closed position.
Figure 13B:
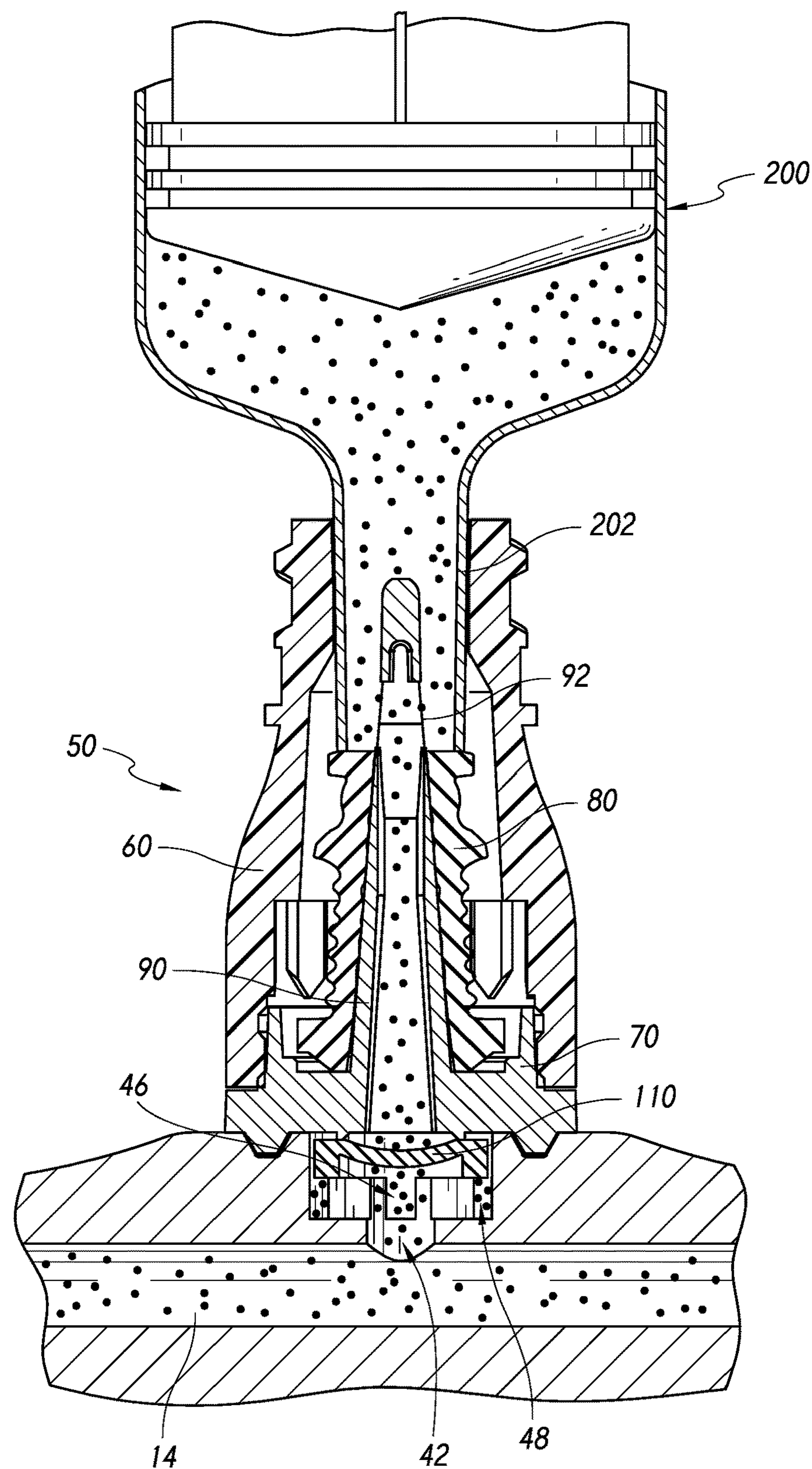
FIG. 13B is a cross-sectional view of the embodiment of FIG. 13A with the check valve in an open position.

FIGS. 13A and 13B illustrate a cross-sectional view of an access port 40 that includes a valve 100 and that has a medical connector attached to the access port. FIGS. 13A and 13B are similar to FIGS. 12A and 12B, but include an illustration of the entirety of a medical connector 50 that can be attached to the access port. Additionally, FIG. 13A illustrates the valve 100 in a closed position and FIG. 13B illustrates a medical implement 200 connected to the medical connector.

As described above, in some embodiments the medical connector 50 can be a needleless connector that has a base 70, a body 60, and a connector valve member 80. The base can also include an internal projection 90 that is within the body 60. A cannula 202 of the medical implement can compress the connector valve member 80 into an open position, exposing an opening 92 in the internal projection through which fluid in the cannula can pass. Once within the internal projection, the fluid can flow into the access port recess 140, through the access channel 42, and into the main flow channel 14. Similar activation can occur with medical connector 50'.

In some embodiments, one or more components of the devices and elements described herein can be translucent, transparent, and/or clear such that the fluid flow path through the components is visible. These components can include, for example, the housing 12 of a manifold, the medical connector 50 (including the body 60, base 70, and/or valve member 80), the medical connector 50' (including the body 60', base 70', and/or valve member 80'), and/or the check valve 100. Additionally, in some embodiments one or more components can include elements configured or adapted to kill pathogens. For example, in some embodiments one or more of the valves 80, 80', or 100 can include antimicrobial agents. In some embodiments, the antimicrobial agents can be a coating or can be incorporated into the structure of the components, from where they can leach out, such as from a silicone matrix of a valve.

The terms "approximately", "about", and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above.

Similarly, this method of disclosure is not to be interpreted as reflecting an intention that any claim require more features than are expressly recited in that claim. Rather, inventive aspects may lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A medical manifold for use in providing access to a fluid flow path, said medical manifold comprising:

a first port;

a second port;

a first channel connecting the first port and the second port and defining a first flow path;

a housing comprising:

a third port comprising a second channel fluidly connecting the third port and the first flow path;

a valve member comprising a diaphragm, the diaphragm comprising a top surface, a bottom surface, and a side wall between the top surface and the bottom surface;

a first support member extending from the bottom surface of the diaphragm and a second support member extending from the bottom surface of the diaphragm, the first support member and the second support member positioned to define a line of symmetry that bisects the bottom surface without passing through the first support member or the second support member, the first support member and the second support member configured to be positioned in the third port to thereby define a space between a bottom wall of the third port and the diaphragm;

a medical connector configured to attach to the third port, wherein the valve member in a closed position is configured to seal against an opening into the medical connector and the valve member in an open position is configured to allow fluid to flow from the medical connector, past the valve member, through the second channel, and into the first flow path;

wherein the diaphragm has a first position in which the top surface is generally planar and is configured to seal against a fluid opening and a second position in which the diaphragm is flexed downward around the line of symmetry thereby creating a concavity on the top surface of the diaphragm, at least a portion of the diaphragm configured to be displaced from the fluid opening in the second position.

2. The medical manifold of claim 1, wherein an outer wall of the third port is cylindrical.

3. The medical manifold of claim 1, wherein an outer wall of the third port comprises multiple walls.

4. The medical manifold of claim 1, wherein the third port further comprises at least two projections extending from the bottom wall of the third port and adjacent the second channel, wherein the at least two projections define an outer channel between the at least two projections and an outer wall of the third port and at least two transverse channels between the at least two projections.

5. The medical manifold of claim 4, wherein the first and second support members are configured to be positioned on at least two of the at least two projections.

6. The medical manifold of claim 1, wherein the valve member is biased toward the closed position.

7. The medical manifold of claim 1, wherein the valve member is configured to move from the closed to the open position as a result of pressure from fluid in the medical connector.

8. The medical manifold of claim 1, wherein the housing is monolithic and includes the first and second ports.

9. The medical manifold of claim 1, wherein a net pressure of less than 3 psi on the valve member is sufficient to move the valve member from the closed position to the open position.

10. The medical manifold of claim 1, wherein the third port further comprises at least two projections extending from the bottom wall of the third port and adjacent the second channel, wherein the at least two projections define at least two transverse channels between the at least two projections.

11. The medical manifold of claim 10, wherein the first and second support members are configured to be positioned on at least two of the at least two projections.

12. The medical manifold of claim 10, wherein the third port includes a recess and the at least two projections extend from a bottom wall of the recess.

13. The medical manifold of claim 12, wherein a wall surrounding the recess extends outward from the housing and a portion of the medical connector is configured to surround at least a portion of the wall surrounding the recess.

14. The medical manifold of claim 13, wherein the medical connector is sonically welded to the third port.

15. The medical manifold of claim 1, wherein the housing further comprises a fourth port comprising a third channel fluidly connecting the fourth port and the first flow path, the manifold further comprising:

a second valve member comprising a diaphragm and a plurality of support members configured to be positioned in the fourth port to thereby define a space between a bottom wall of the fourth port and the diaphragm; and a second medical connector configured to attach to the fourth port, wherein the second valve member in a closed position is configured to seal against an opening into the second medical connector and the second valve member in an open position is configured to allow fluid to flow from the second medical connector, past the second valve member, through the third channel, and into the first flow path.

16. The medical manifold of claim 1, wherein the first port is configured to engage a medical luer connector.

17. The medical manifold of claim 1, wherein the manifold further comprises:

a second housing comprising a fourth port with a third channel fluidly connecting the fourth port and the first flow path;

a second valve member comprising a diaphragm and a plurality of support members configured to be positioned in the fourth port to thereby define a space between a bottom wall of the fourth port and the diaphragm; and a second medical connector configured to attach to the fourth port, wherein the second valve member in a closed position is configured to seal against an opening into the second medical connector and the second valve member in an open position is configured to allow fluid to flow from the second medical connector, past the second valve member, through the third channel, and into the first flow path.

18. The medical manifold of claim 17, wherein the first and second housings are monolithic.

19. The medical manifold of claim 17, wherein the first and second housings are joined by a flexible connecting element.

* * * * *